(12) United States Patent
Zhang et al.

(10) Patent No.: US 8,679,849 B2
(45) Date of Patent: Mar. 25, 2014

(54) METHOD AND DEVICE FOR DETECTION OF HEAVY METAL IONS IN WATER

(75) Inventors: Xiaoke Zhang, Shanghai (CN); Hisashi Kajiura, Tokyo (JP); Yongming Li, Tokyo (JP)

(73) Assignee: Sony Corporation, Tokyo (JP)

( * ) Notice: Subject to any disclaimer, the term of this patent is extended or adjusted under 35 U.S.C. 154(b) by 246 days.

(21) Appl. No.: 13/348,206

(22) Filed: Jan. 11, 2012

(65) Prior Publication Data
US 2012/0184040 A1    Jul. 19, 2012

(30) Foreign Application Priority Data

Jan. 19, 2011  (CN) .......................... 2011 1 0021678

(51) Int. Cl.
*G01N 33/20* (2006.01)
(52) U.S. Cl.
USPC ............ 436/80; 436/81; 436/73; 210/500.27; 210/500.1
(58) Field of Classification Search
USPC ................. 436/73, 80, 81; 210/500.27, 500.1
See application file for complete search history.

(56) References Cited

U.S. PATENT DOCUMENTS 7,988,854 B2 * 8/2011 Tsukamoto .............. 210/321.71
2011/0020943 A1 * 1/2011 Okamoto et al. .............. 436/73

OTHER PUBLICATIONS

Chemical modification of silica surface by immobilization of functional groups for extractive concentration of metal ions P.K. Jal, S. Patel, B.K. Mishra Talanta 62 (2004) 1005-1028.*

* cited by examiner

*Primary Examiner* — Krishnan S Menon
*Assistant Examiner* — Dwan A Gerido
(74) *Attorney, Agent, or Firm* — K&L Gates LLP

(57) ABSTRACT

This disclosure discloses a method and a device for the detection of heavy metal ions in water. The method includes: providing a detection material, wherein the detection material includes a hydrophilic layer which is at least partially covered by a hydrophobic layer formed from a long-chain compound selected from the group consisting of a long-chain thiol, a long-chain fatty acid and combinations thereof, and wherein a detection area is an area covered by the hydrophobic layer, and the detection area has a surface having an initial contact angle with water of more than or equal to about 120°; contacting the detection area with an aqueous solution sample; determining whether the surface of the detection area has a hydrophobicity-hydrophilicity change after contact with the aqueous solution sample; and deciding whether heavy metal ions exist in the aqueous solution sample according to the determination.

21 Claims, 13 Drawing Sheets ic layer, and the area has a surface having an initial contact angle with water of more than or equal to about 120°.

METHOD AND DEVICE FOR DETECTION OF HEAVY METAL IONS IN WATER

CROSS REFERENCES TO RELATED APPLICATIONS

The present application claims priority to Chinese Patent Application No. 201110021678.4 filed on Jan. 19, 2011, the disclosure of which is incorporated herein by reference.

BACKGROUND

The present application relates to a method and a device for the detection of heavy metal ions in water. More specifically, the present application relates to a method for the detection of lead (Pb), mercury (Hg) and cadmium (Cd), or heavy metal ions of other types in aqueous solution employing a detection material, and a device for the detection of heavy metal ions in water based on the method.

Heavy metal ions, in particular those at a certain concentration, can lead to heavy metal poisoning, which causes illness or toxicity to human, such as dysfunction of nerve system, change in blood composition, heart and lung diseases, and the like. In recent years, analytical method and isolation technique have been developed to identify heavy metal contamination.

A variety of methods, including atomic absorption spectrometry, inductively coupled plasma-mass spectrometry, spectrophotometry (e.g., based on heavy metal-dithizone chelation) and electrochemical methods (e.g., anodic stripping analysis) have been widely used for quantitatively detecting heavy metal ions with micro even trace concentration. However, most of these methods have been limited by, for example, the need for expensive instruments, laboratory apparatus, high operating cost and/or expertise on analytical technique from the personnel.

Strip test is one of the most simple and economic methods for the semi-quantitative detection of heavy metal ions in aqueous solution. The strip test mechanism is that heavy metal chromogenic agents (such as dithizone and the like) form complexes with various types of heavy metal ions, which exhibit different colors, and the colors and the tone correlate with the concentrations of the heavy metal ions. For example, a test strip using dithizone as a heavy metal chromogenic agent can semi-quantitatively detect $Cd^{2+}$ (also referred to as Cd(II) herein), $Pb^{2+}$ (also referred to as Pb(II) herein) and $Hg^{2+}$ (also referred to as Hg(II) herein), and the like. However, these heavy metal chromogenic agents not only chelate the heavy metal ions, but also complex with other ions such as $Ca^{2+}$ (also referred to as Ca(II) herein), $Mg^{2+}$ (also referred to as Mg(II) herein) or $Fe^{3+}/Fe^{2+}$ (also referred to as Fe(III)/Fe(II) herein), and the like. Therefore, when detecting heavy metal ions such as Cd(II), Pb(II) and Hg(II), and the like, many masking agents are required to prevent the reaction between dithizone with the non-heavy metal ions in the system, which complicates the experimental operation. Moreover, some of the masking agents are very toxic chemicals (such as potassium cyanide).

Therefore, developing a highly efficient detection system which is not only sensitive and reliable but also simple, convenient, economical and practical as well as suitable for the in situ detection of heavy metal ions in common aqueous environments is actually more and more desirable. There is still a desire for a new method or material which can safely and simply detect heavy metal ions in aqueous solution.

SUMMARY

The present application provides a cheap, simple and safe method for the detection of heavy metal ions in an aqueous solution sample according to an embodiment.

An aspect of the present application is to provide a method for the detection of heavy metal ions in aqueous solution, including: providing a detection material, wherein the detection material includes a hydrophilic layer which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, and the area has a surface having an initial contact angle with water of more than or equal to about 120°; contacting the detection area of the detection material with an aqueous solution sample; determining whether the surface of the detection area of the detection material has a hydrophobicity-hydrophilicity change after the area is contacted with the aqueous solution sample; and deciding whether heavy metal ions exist in the aqueous solution sample according to the determination.

By using the method of the present application, complicated pre-treatment is not needed for the detection of heavy metal ions, including, but not limited to $Zn^{2+}$, $Cu^{2+}$ (also referred to as Cu(II) herein), $Cd^{2+}$, $Pb^{2+}$, $Ag^+$, $Hg^{2+}$ and $Hg_2^{2+}$ (also referred to as $Hg_2$(II) herein); in particular, for the detection of the common heavy metal ions highly hazardous to human body such as ions of lead (Pb), mercury (Hg) and cadmium (Cd). Hg(II) (lowest detectable limit at least about $1\times10^{-7}$ M), $Hg_2$(II) (lowest detectable limit at least about $1\times10^{-7}$ M), Pb(II) lowest detectable limit at least about $1\times10^{-6}$ M), Cd(II) (lowest detectable limit at least about $1\times10^{-6}$ M), Cu(II) (lowest detectable limit at least about $1\times10^{-5}$ M), and Zn(II) (lowest detectable limit at least about $1\times10^{-5}$ M) can be detected within 15 minutes, or several types of heavy metal ions (total concentration $\geq\sim1\times10^{-6}$ M) can be detected simultaneously without the need of complicated pre-treatment, even in case that non-heavy metal ions such as $K^+$ (also referred to as K(I) herein), $Na^+$ (also referred to as Na(I) herein), Mg(II), and Ca(II) exist in the aqueous solution sample.

Another aspect of the present application is to provide a device for the detection of heavy metal ions in aqueous solution including a main body and a detection material, wherein the detection material includes a hydrophilic layer which is at least partially covered by a hydrophobic layer formed from a long-chain compound selected from the group consisting of a long-chain thiol, a long-chain fatty acid and combinations thereof, wherein an area covered by the hydrophobic layer is defined here as a detection area, and the area has a surface having an initial contact angle with water of more than or equal to about 120°, and wherein the detection area of the detection material may be exposed in the exterior of the main body for contacting with the aqueous solution.

Another aspect of the present application is to provide a detection kit including the device of the present application and a container filled with a colorant solution.

Another aspect of the present application is to provide a use of a detection material for the detection of heavy metal ions in aqueous solution, wherein the detection material includes a hydrophilic layer, which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°.

A method for the detection of heavy metal ions in aqueous solution is provided. The method includes, in an embodiment, providing a detection material, wherein the detection material includes a hydrophilic layer which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°; contacting the detection area of the detection material with an aqueous solution sample; determining whether the surface of the detection area of the detection material has a hydrophobicity-hydrophilicity change after the area is contacted with the aqueous solution sample; and deciding whether heavy metal ions exist in the aqueous solution sample according to the determination.

According to an embodiment, the hydrophilic layer includes a nanomaterial layer.

According to an embodiment, the hydrophilic layer is formed from a metal oxide, preferably a zinc oxide.

According to an embodiment, the detection material further includes a substrate which is at least partially and preferably completely covered by the hydrophilic layer.

According to an embodiment, the substrate includes a conductive substrate.

According to an embodiment, the hydrophilic layer is completely covered by the hydrophobic layer.

According to an embodiment, the detection material includes a metal substrate which is at least partially covered by a hydrophilic layer which is at least partially covered by a hydrophobic layer, wherein the hydrophilic layer is formed from a metal oxide and the hydrophobic layer is formed from a long-chain compound selected from a long-chain thiol, a long-chain fatty acid and combinations thereof, and wherein a detection area is defined by an area covered by the hydrophobic layer, which has a surface having an initial contact angle with water of more than or equal to about 120°.

According to an embodiment, the metal substrate is selected from a metal zinc substrate.

According to an embodiment, the metal oxide is selected from a zinc oxide.

According to an embodiment, the hydrophilic layer is completely covered by the hydrophobic layer.

According to an embodiment, the metal substrate is completely covered by the hydrophilic layer.

According to an embodiment, the detection area has a surface having an initial contact angle with water of more than or equal to about 150°.

According to an embodiment, the long-chain compound is at least one selected from the long-chain thiols having 8-20 carbon atoms.

According to an embodiment, the long-chain compound is at least one selected from the n-alkyl thiols having 8-20 carbon atoms.

According to an embodiment, the long-chain compound is at least one selected from n-octyl thiol, n-dodecyl thiol, n-hexadecyl thiol and n-octadecyl thiol.

According to an embodiment, the method further includes adding a solubilizer into the aqueous solution sample before or during contacting the detection area of the detection material with the aqueous solution sample.

According to an embodiment, the solubilizer includes a water soluble alcohol.

According to an embodiment, the solubilizer is at least one selected from methanol, ethanol and propanol.

According to an embodiment, the method further includes treating the detection material by applying a voltage to the detection material during the contacting of the detection area of the detection material with the aqueous solution sample, wherein the detection material is conductive.

According to an embodiment, the method further includes immersing the detection area of the detection material into a colorant solution after the area is contacted with the aqueous solution sample, and carrying out the determining of whether the surface of the detection area of the detection material has a hydrophobicity-hydrophilicity change by observing whether color change occurs on the surface of the detection area.

According to an embodiment, the heavy metal ion includes one or more of $Zn^{2+}$, $Cu^{2+}$, $Cd^{2+}$, $Pb^{2+}$, $Ag^+$, $Hg^{2+}$ and $Hg_2^{2+}$.

A device for the detection of heavy metal ions in aqueous solution including a main body and a detection material, wherein the detection material includes a hydrophilic layer, which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°; and wherein the detection area of the detection material may be exposed in the exterior of the main body for contacting with the aqueous solution.

According to an embodiment, the detection material includes a metal substrate and a hydrophilic layer on the substrate, which is at least partially covered by a hydrophobic layer, wherein the hydrophilic layer is formed from a metal oxide and the hydrophobic layer is formed from a long-chain compound selected from a long-chain thiol, a long-chain fatty acid and combinations thereof, and wherein a detection area is defined by an area covered by the hydrophobic layer, which has a surface having an initial contact angle with water of more than or equal to about 120°.

According to an embodiment, the detection area has a surface having an initial contact angle with water of more than or equal to about 150°.

A detection kit, including the device described above and a container filled with colorant solution.

According to an embodiment, the detection kit further includes electrolysis device and/or a container filled with a solubilizer.

Use of a detection material for the detection of heavy metal ions in aqueous solution, wherein the detection material includes a hydrophilic layer, which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°.

The present application provides a low-cost, simple and practical way of in situ qualitatively detecting heavy metal ions in water.

Additional features and advantages are described herein, and will be apparent from the following Detailed Description and the figures.

DETAILED DESCRIPTION

Figure 1:
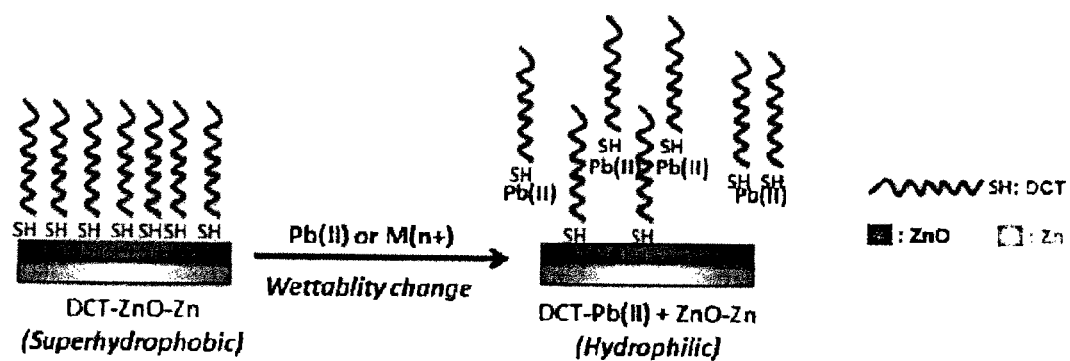
FIG. 1 shows the mechanism of detecting Pb(II) or other types of heavy metal ions by using superhydrophobic zinc sheet.

Embodiments of the present application will be described below in detail with reference to the drawings.

Unless expressly indicated otherwise, the term "a", "an" and "the" does not mean one, and encompasses the plural forms. Endpoints of all ranges representing the same feature or component are included or can be independently combined. The terms "first", "second", and the like are not to represent any order, quantity or importance, but to distinguish one element from another.

Method for the Detection of Heavy Metal Ions in Aqueous Solution

One aspect of the present application is directed to a method for the detection of heavy metal ions in aqueous solution, including: providing a detection material, wherein the detection material includes a hydrophilic layer which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°; contacting the detection area of the detection material with an aqueous solution sample; determining whether the surface of the detection area of the detection material has a hydrophobicity-hydrophilicity change after the area is contacted with the aqueous solution sample; and deciding whether heavy metal ions exist in the aqueous solution sample according to the determination.

The method of the present application is implemented by detecting the hydrophobicity-hydrophilicity change on the surface of the detection area of the detection material caused by the reaction between the detection area and the heavy metal ions in the aqueous solution sample.

Providing Detection Material

The hydrophobicity or hydrophilicity of solid material reflects the wettability of the surface of the material by liquid and can be measure by the contact angles (CA) with water. Usually, the range of contact angles is between 0° and 180°. In general, a surface with a contact angle with water from 0° to 90° is called a hydrophilic surface; a surface with a contact angle with water of more than 90° is called a hydrophobic surface; and a surface with a contact angle with water of more than 150° is called a superhydrophobic surface.

The detection material used in the present application includes a hydrophilic layer which is at least partially covered by a hydrophilic layer, wherein a detection area is defined by an area covered by the hydrophobic layer, which has a surface having an initial contact angle with water of more than or equal to about 120°. In the detection material of the present application, the detection area refers to the area covered by the hydrophobic layer, including the hydrophilic layer covered by the hydrophobic layer and the hydrophobic layer covering the hydrophilic layer. The hydrophobic layer is used as the surface of the detection area for contacting with the aqueous solution sample during detection. The term "the initial contact angle with water of the surface of the detection area" as used herein refers to the contact angle between the hydrophobic layer surface of the detection area and water before the detection employing the method of the present application.

When the method of the present application is performed, the hydrophobic layer of the detection area may be disrupted by the heavy metal ions existing in the aqueous solution so as to cause hydrophobicity-hydrophilicity changes in the detection area. If the occurrence of hydrophobicity-hydrophilicity changes in the detection area is detected, it can be determined that a certain concentration of heavy metal ions exist in the aqueous solution sample. If not, it indicates that heavy metal ions do not exist in the aqueous solution sample, or its concentration is very low (e.g., lower than the lowest detectable limit).

Figure 13:
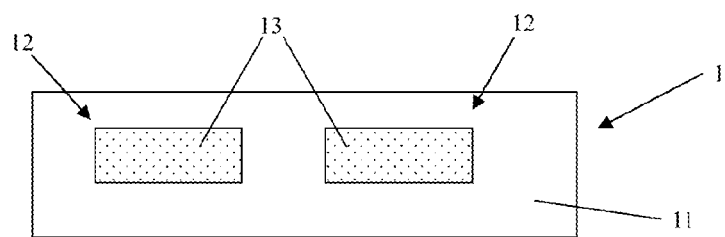
FIG. 13 is a diagram of the detection material according to one embodiment.

FIG. 13 shows a diagram of the detection material according to one embodiment. As shown in FIG. 13, the detection material 1 includes the hydrophilic layer 11 which is at least partially covered by the hydrophobic layer 13, and the detection area 12 includes the hydrophobic layer 13 and the hydrophilic area covered by the hydrophobic layer 13. The hydrophobic layer 13 is the surface of the detection area 12.

The hydrophilic layer of the detection material of the present application is at least partially covered by the hydrophilic layer. The term "at least partially covered by" as used herein includes "partially covered by" and "completely covered by".

In one embodiment, the hydrophilic layer is partially covered by the hydrophobic layer in the detection material of the present application.

In another embodiment, the hydrophilic layer is completely covered by the hydrophobic layer. The term "the hydrophilic layer being completely covered by the hydrophobic layer" as used herein may include "at least one plane of the hydrophilic layer of the detection material being completely covered by the hydrophobic layer", in that case the hydrophobic layer that completely covers the at least one plane of the hydrophilic layer becomes the surface of the detection area. The term "the hydrophilic layer being completely covered by the hydrophobic layer" as used herein may also include "all planes of the hydrophilic layer of the detection material being completely covered by the hydrophobic layer", in that case the hydrophobic layer that completely covers all planes of the hydrophilic layer becomes the surface of the detection area.

In one embodiment, the hydrophilic layer of the detection material of the present application includes a nanomaterial layer. The term "nanomaterial" as used herein refers to a layer formed by a material with dimensions of nanometer range. The nanomaterial may have at least one dimension from several to several hundred nanometers. The nanomaterial layer may be an array formed from a nanowire or a nanorod or the like (nanoarray), where the nanowire or nanorod may have a diameter of about 2 to 500 nanometers, preferably 20 to 300 nanometers, and more preferably about 30 to 200 nanometers. Alternatively, the nanomaterial layer may be a layer formed from a nanoparticle. Any known nanomaterial in the art may be used to form the nanomaterial layer, insomuch that the resultant nanomaterial layer is hydrophilic. Examples of nanomaterials that can be used in the present application include, but are not limited to, nano metal oxides, hydrophilic metal materials, and the like In one embodiment, the hydrophilic layer may be formed from a metal oxide. Any know metal oxide in the art can be used, insomuch that the layer formed by such an oxide is hydrophilic. The metal oxides may include an oxide of a single metal or an oxide of a metal alloy. In one embodiment, the examples of oxides of a single metal include, but are not limited to, e.g., zinc oxide, cupric oxide, and the like In another embodiment, the examples of oxides of a metal alloy include, but are not limited to, an oxide of zinc-copper and the like. In one embodiment, the metal oxide is a nanometer metal oxide, e.g., a metal oxide nanowire or nanorod having a diameter of about 2 to 500 nanometers, preferably about 20 to 300 nanometers, and more preferably about 30 to 200 nanometers.

The thickness of the hydrophilic layer can be varied if necessary. In one embodiment, the hydrophilic layer may have a thickness of about 20 nanometers to 20 micrometers. In another embodiment, the hydrophilic layer may have a thickness of about 100 nanometers to 10 micrometers. In another embodiment, the hydrophilic layer may have a thickness of about 1 to 5 micrometers.

In another embodiment, the detection material of the present application further includes a substrate which is at least partially covered by the hydrophilic layer. The substrate serves as a carrier to hold the hydrophilic layer, or if desired, can provide a conductive circuit for the detection material, and can simplify the preparation of the detection material.

The term "the substrate being at least partially covered" as used herein includes "the substrate being partially covered" and "the substrate being completely covered".

In one embodiment, only substrate is covered by the hydrophilic layer in the detection material of the present application.

In another embodiment, the substrate is completely covered by the hydrophilic layer. The term "the substrate being completely covered by the hydrophilic layer" as used herein may include "at least one plane of the substrate of the detection material being completely covered by the hydrophilic layer". The term "the substrate being completely covered by the hydrophilic layer" as used herein may also include "all planes of the substrate of the detection material being completely covered by the hydrophilic layer".

The material that may serve as the substrate includes a conductive material and a non-conductive material. In one embodiment, the conductive material that serve as the substrate includes a conductive metal material and a conductive non-metal material. In one embodiment, the conductive non-metal material includes, but is not limited to, e.g., ITO (indium tin oxide) and the like. In another embodiment, the metal material includes, but is not limited to, gold, silver, platinum, palladium, copper, titanium, aluminum, tin, zinc, or alloys thereof, and the like. When a conductive substrate is needed, a metal can serve as the substrate, or alternatively, a non-metal substrate with its surface covered by a conductive metal film such as a gold film can serve as the conductive substrate.

In another embodiment, exemplified the non-conductive material that serve as the substrate include silicon, quartz, a polymer material such as PET, polytetrafluoroethylene, high-density polyethylene, organosilicon, fluoropolymer, and the like.

In an embodiment according to the present application, the substrate is produced from a conductive material. This is because as described below, electric treatment can be employed to accelerate the detection and increase the sensitivity of the detection.

Figure 14:
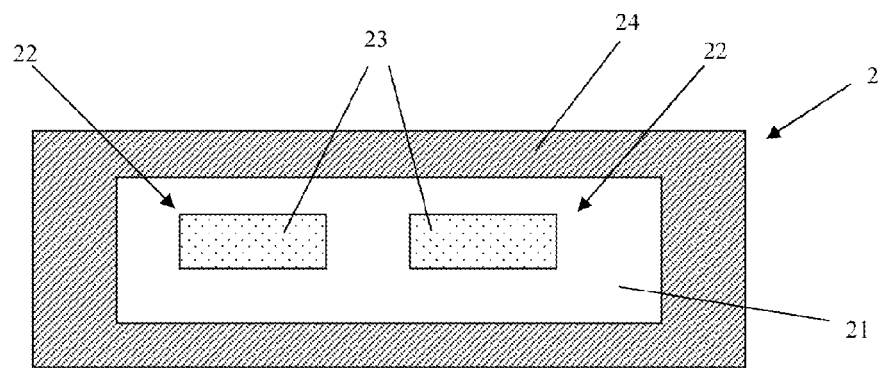
FIG. 14 is a diagram of the detection material according to another embodiment.

FIG. 14 is a diagram illustrating the detection material of another embodiment. As shown in FIG. 14, the detection material 2 includes the substrate 24, which is at least partially covered by the hydrophilic layer 21, which is at least partially covered by the hydrophobic layer 23, and the detection area 22 includes the hydrophobic layer 23 and the hydrophilic area covered by the hydrophobic layer 23, and the hydrophobic layer 23 is the surface of the detection area 22.

Although as illustrated in FIGS. 13 and 14, the detection material includes two detection areas (12) and (22). However, it is appreciated by a person skilled in the art that the detection material of the present application may include one or more detection areas.

In one embodiment, there may be one detection area. The one detection area may locate at the end or edge of the detection material so as to facilitate the detection area of the detection material to contact with the aqueous solution sample to be tested. Alternatively, if necessary, the one detection area can locate at another site of the detection material.

In another embodiment, the detection area may be more than one, e.g., at least 2, at least 3, at least 4, or 5 or more. Several detection areas are arranged in the detection material so as to achieve multiple measurements on the aqueous solution sample to be tested within one detection process, thereby ensuring the accuracy of the detection result. Arrangement of several detection areas in the detection material can also make the detection material to be used for multiple times so as to save the detection material. The several detection areas can be arranged in various ways. For example, the several detection areas can be arranged in the form of an array. The several detection areas can also be arranged in the form of a strip.

In the embodiment in which there are several detection areas of the detection material, the surfaces of various detection areas may have the same or different initial contact angles with water. For example, the surfaces of various detection areas may have the same contact angle with water (alternatively, the difference in initial contact angles is within 10%, or 5%, or 2%). The surfaces of various detection areas may have different contact angles with water (e.g., the difference in initial contact angles is more than about 2%, or more than about 5%, or more than about 10%). Alternatively, the detection areas may be classified into different groups according to their initial contact angles with water, wherein the surfaces of the detection areas in each group may have the same initial contact angles with water (alternatively, alternatively, the difference in initial contact angles is within 10%, or 5%, or 2%), and the surfaces of the detection areas between different groups have different initial contact angles with water (e.g., the difference in initial contact angles is more than about 2%, or more than about 5%, or more than about 10%). If necessary, the several detection areas may be adjacent to each other, or separated with each other for a certain distance.

Although the detection areas (12) and (22) of the detection material are illustrated in a planar rectangular form in FIGS. 13 and 14, it should be appreciated by a person skilled in the art that the detection areas may have any other shape. A person skilled in the art may decide the size and/or shape of a detection area if necessary, as long as the size and shape of the detection area is suitable for the method according to the present application. For example, the detection area may have a rectangular, square, circular, elliptic, strip, irregular, or curved shape.

In one embodiment, the detection material may be designed as a sheet. The detection material includes a hydrophilic sheet, whose two planes can both at least be partially covered by a hydrophobic layer. Therefore, areas covered by a hydrophobic layer, i.e., the detection areas, may be formed on both planes of the detection material.

In another embodiment, the detection material may be designed as a sheet. The detection material includes a substrate sheet and a hydrophilic layer which at least partially (preferably completely) covers one or more surfaces of the substrate sheet. The hydrophilic layer may at least partially be covered by a hydrophobic layer so as to form an area covered by a hydrophobic layer, i.e., the detection area.

In one embodiment, the detection material may be designed as a rod. The detection material includes rod-shaped hydrophilic material which may at least partially be covered by a hydrophobic layer, thereby forming an area covered by a hydrophobic layer, i.e., the detection area.

In another embodiment, the detection material may be designed as a rod. The detection material includes a rod-shaped core which is at least partially covered by a hydrophilic layer, and the hydrophilic layer is at least partially covered by a hydrophobic layer, thereby forming an area covered by a hydrophobic layer, i.e., the detection area.

The detection material may also be designed as having, e.g., spherical, ellipsoidal and other shapes, such as comb, if necessary.

Considering factors such as convenience of use, and the like, the detection material of the present application may be designed as a sheet or a rod.

In one embodiment of the present application, the detection material of the present application includes a substrate which is at least partially (preferably completely) covered by a hydrophilic layer, and the hydrophilic layer at least partially covered by a hydrophobic layer (preferably, which is completely covered by the hydrophobic layer), a detection area is defined by an area covered by the hydrophobic layer, which has a surface having an initial contact angle with water of more than or equal to about 120°, wherein the hydrophobic layer is formed from a long-chain compound selected from the group consisting of a long-chain thiol, a long-chain fatty acid and combinations thereof.

In one embodiment, the detection material includes a metal substrate which is at least partially (preferably completely) covered by a hydrophilic layer, and the hydrophilic layer is at least partially covered by a hydrophobic layer (preferably, which is completely covered by the hydrophobic layer), wherein the hydrophilic layer is formed from a metal oxide, the hydrophobic layer is formed from a long-chain compound selected from the group consisting of a long-chain thiol, a long-chain fatty acid and combinations thereof, and a detection area is defined by an area covered by the hydrophobic layer, which has a surface having an initial contact angle with water of more than or equal to about 120°, preferably, a surface having an initial contact angle with water of more than or equal to about 150°. In the embodiment, the metal in the metal oxide may be the same or different metal from the metal in the metal substrate. Preferably, the metal oxide may be an oxide of the metal in the metal substrate.

In one embodiment, the thickness of the hydrophilic layer formed from the metal oxide is about 20 nanometers to 20 micrometers, preferably about 100 nanometers to 10 micrometers, and more preferably about 0.5 to 5 micrometers.

The formation of the hydrophilic layer that at least partially covers a substrate (especially a metal substrate) can be carried out according to a method known to a person skilled in the art, e.g., etching, sol-gel method, template method, pyrolysis, chemical vapor deposition, electrochemical method, chemical method, self-assembly growth method, gas transportation method, thermal evaporation method, and the like. A person skilled in the art can choose a suitable method if necessary.

In one embodiment, the hydrophilic layer that at least partially covers a metal substrate, especially the hydrophilic layer that completely covers the metal substrate, can be formed by oxidation, wherein the hydrophilic layer can be formed by a metal oxide. Preferably, the metal oxide is a nano metal oxide.

In another embodiment, the hydrophilic layer that at least partially covers a substrate (especially a metal substrate) can be formed by chemical vapor deposition. Preferably, the hydrophilic layer is formed from a metal oxide.

In an embodiment, the detection material used in the method of the present application includes a metal zinc substrate which is at least partially covered by a hydrophilic layer formed from zinc oxide, which is at least partially covered by a hydrophobic layer formed from a long-chain compound selected from the group consisting of a long-chain thiol, a long-chain fatty acid and combinations thereof, a detection area is defined by an area covered by the hydrophobic layer, which has a surface having an initial contact angle with water of more than or equal to about 120°, preferably, a surface having an initial contact angle with water of more than or equal to about 150°.

In the detection material of the present application, the hydrophobic layer that at least partially covers the hydrophilic layer is formed from a long-chain compound selected from the group consisting of a long-chain thiol, a long-chain fatty acid and combinations thereof. The term "long-chain thiol" as used herein refers to a thiol having the chain length of 6 carbon atoms or more. The term "long-chain fatty acid" as used herein refers to an aliphatic carboxylic acid having the chain length of 6 carbon atoms or more.

In an embodiment, the long-chain thiol is selected from a long-chain thiol having the chain length of about 8-20 carbon atoms, preferably about 10-20 carbon atoms, and more preferably about 12-18 carbon atoms.

In an embodiment, the long-chain fatty acid is selected from a long-chain fatty acid having the chain length of about 8-20 carbon atoms, preferably about 10-20 carbon atoms, and more preferably about 12-18 carbon atoms.

In an embodiment, the long-chain compound is selected from one or more of the long-chain thiol having the chain length of about 8-20 carbon atoms, preferably about 10-20 carbon atoms, and more preferably about 12-18 carbon atoms, because a thiol has relatively stronger coordinative capacity with heavy metal ions so as to increase the sensitivity and speed of the method according to the present application. In an embodiment according to the present application, the long-chain thiol is selected from one or more of long-chain n-alkyl thiol having about 8-20 carbon atoms. Examples include, but are not limited to, n-octyl thiol, n-dodecyl thiol, n-hexadecyl thiol and n-octadecyl thiol.

The formation of the hydrophobic layer from the long-chain compound may be carried out by self-assembly, spin-coating, casting, and the like, wherein the long-chain compound is selected from the group consisting of a long-chain thiol, a long-chain fatty acid and combinations thereof.

In one embodiment, the hydrophobic layer can be formed from the long-chain compound by self-assembly, thereby preparing the detection material of the present application, wherein the long-chain compound is selected from the group consisting of a long-chain thiol, a long-chain fatty acid and combinations thereof. For example, the self-assembly can be performed as follows: the material including the hydrophilic layer and an optional substrate (wherein the optional substrate is at least partially covered by the hydrophilic layer) is immersed in the solution of the long-chain compound (the long chain compound is selected from the group consisting of a long-chain thiol, a long-chain fatty acid and combinations thereof), and maintained for a certain time to enable the formation the hydrophobic layer that covers the hydrophilic layer, wherein the area covered by the hydrophilic layer is called the detection area. The solvent used in the solution of the long-chain compound can include a known solvent in the art, such as an alcohol (such as ethanol, methanol and propanol) and the like.

In the detection material used in the present application, the detection area has a surface having an initial contact angle with water CA≥about 120°. In another embodiment, the detection area has a surface having an initial contact angle with water CA≥about 130°, and preferably ≥about 140°. In an embodiment, the detection area has a surface having an initial contact angle with water CA≥about 150°, in that case the detection area has superhydrophobicity.

A person skilled in the art can properly select the variety and concentration of the long-chain compound used, the variety of the solvent, and the conditions of self-assembly according to the desired surface hydrophobicity (i.e., the initial contact with water) of the detection area, wherein the long chain compound is selected from the group consisting of a long-chain thiol, a long-chain fatty acid and combinations thereof.

In one embodiment, the long-chain compound may have a concentration of about 0.1 to 100 mmol/L. In another embodiment, the long-chain compound may have a concentration of about 0.5 to 50 mmol/L.

In one embodiment, the self-assembly may usually be carried out at room temperature. In another embodiment, the self-assembly may be carried out for about 1 hour to 200 hours, e.g., about 5 hours to 100 hours.

The preparation of the detection material of the present application may include: firstly, providing a the material including the hydrophilic layer and an optional substrate (wherein the optional substrate is at least partially covered by the hydrophilic layer); secondly, forming a hydrophobic layer that at least partially covers the hydrophilic layer with the long chain compound, which is selected from the group consisting of a long-chain thiol, a long-chain fatty acid and combinations thereof, thereby obtaining the detection material of the present application, wherein the area covered by the hydrophilic layer is called the detection area, which has a surface having an initial contact angle with water of more than or equal to about 120°, preferably, more than or equal to about 150°.

In one embodiment, a material including a hydrophilic layer and a substrate is provided, wherein the substrate is at least partially covered by the hydrophilic layer. As mentioned above, the hydrophilic that at least partially covers the substrate may be formed according to a method known to a person skilled in the art, such as etching, sol-gel method, template method, pyrolysis, chemical vapor deposition, electrochemical method, chemical method, self-assembly growth method, gas transportation method, thermal evaporation method, and the like. In one embodiment, the hydrophilic layer can be formed from a metal oxide, preferably zinc oxide, by oxidation.

In one embodiment, a material including a hydrophilic layer and a substrate can be formed as follows: a non-metal substrate (such as indium tin oxide (ITO) is heated in a mixed system of $Zn(NO_3)_2$, $(CH_2)_6N_4$ or urea so that a ZnO nanometer crystal can form on the non-metal substrate (such as indium tin oxide (ITO), thereby forming a material including a hydrophilic layer and a substrate.

Preparing the detection material also includes forming a hydrophobic layer that at least partially covers the hydrophilic layer from the long-chain compound, which is selected from the group consisting of a long-chain thiol, a long-chain fatty acid and combinations thereof. As mentioned above, the hydrophobic layer may be formed by a self-assembly technique, wherein the hydrophobic layer is a self-assembled monolayer (SAM) of the long-chain compound, which is selected from the group consisting of a long-chain thiol, a long-chain fatty acid and combinations thereof. The long-chain compound is preferably selected from one or more of a long-chain thiol having about 8-20 carbon atoms, preferably about 10-20 carbon atoms, and more preferably about 12-18 carbon atoms; more specifically, the long-chain compound preferably is selected from one or more of a long-chain n-alkyl thiol having about 8-20 carbon atoms; and further preferably, the long-chain compound preferably is selected from one or more of n-octyl thiol, n-dodecyl thiol, n-hexadecyl thiol and n-octadecyl thiol.

In one embodiment, the (super)hydrophobic zinc sheet that can serves as the detection material of the present application can be prepared as follows: (1) The zinc sheet is immersed in an oxidation solution for oxidation, thereby forming a hydrophilic ZnO layer around the zinc sheet that covers the zinc sheet; (2) Subsequently, the ZnO layer of the resultant material is immersed into a solution of one or more the long-chain compounds so that a self-assembled monolayer (hydrophobic layer) of one or more the long-chain compounds can form. The self-assembled monolayer may exhibit (super)hydrophobicity, and at least partially cover the hydrophilic layer (ZnO layer), wherein the area covered by the hydrophobic layer is called the detection area, which has a surface having an initial contact angle with water of more than or equal to about 120°, preferably, more than or equal to about 150°; thereby obtaining the (super) hydrophobic zinc sheet that can serve as the detection material of the present application.

In the above embodiment, "the zinc sheet being immersed in an oxidation solution for oxidation" includes "the zinc sheet being completely immersed in an oxidation solution for oxidation" and "the zinc sheet being partially immersed in an oxidation solution for oxidation". In case that the zinc is completely immersed in the oxidation solution, the ZnO layer that completely covers the metal zinc sheet can be obtained. In case that the zinc is partially immersed in the oxidation solution, the ZnO layer that partially covers the metal zinc sheet can be obtained.

In the above embodiment, "the ZnO layer of the resultant material being immersed into a solution of one or more the long-chain compounds" includes "the ZnO layer of the resultant material being completely immersed into a solution of one or more the long-chain compounds" and "the ZnO layer of the resultant material being partially immersed into a solution of one or more the long-chain compounds". In case that the ZnO layer of the resultant material is completely immersed into the solution, a hydrophobic layer that completely covers the hydrophilic layer can form. In case that the ZnO layer of the resultant material is partially immersed into the solution, a hydrophobic layer that partially covers the hydrophilic layer can form.

In some embodiments, examples of the oxidation solution include, but are not limited to, N,N-dimethylacetamide-water mixture and formamide-water mixture. In another embodiment, 0.5%~20% (volume), preferably 2%~15% (volume) N,N-dimethylacetamide-water mixture is used as the oxidation solution. In another embodiment, 0.5%~20% (volume), preferably 2%~15% (volume) N,N-formamide-water mixture is used as the oxidation solution. The appropriate oxidation conditions may be chosen by a person skilled in the art if necessary. In one embodiment, the oxidation may be carried out at 20 to 100° C., especially 30 to 80° C. In another embodiment, the oxidation may be carried out for 0.5 hour to 100 hours, especially 2 hours to 50 hours.

As mentioned above, the long-chain compound is preferably selected from one or more of a long-chain thiol having about 8-20 carbon atoms; more specifically, the long-chain compound preferably is selected from one or more of a long-chain n-alkyl thiol having about 8-20 carbon atoms; and further preferably, the long-chain compound preferably is selected from one or more of n-octyl thiol, n-dodecyl thiol, n-hexadecyl thiol and n-octadecyl thiol. The solvent used can include a known solvent in the art, such as an alcohol (such as ethanol, methanol and propanol), or the like.

In another embodiment, the immersed zinc sheet can completely be oxidized into ZnO by selecting a zinc sheet of proper thickness and the oxidation conditions (such as the variety and/or concentration of the oxidation solution, temperature, duration, and the like); subsequent to immersing the ZnO layer into a solution of one or more the long-chain compounds is carried out in which the resultant material (hydrophilic ZnO material) is completely or partially immersed into a solution of one or more of the long-chain compounds, so that a self-assembled monolayer (the hydrophobic layer) of the one or more of the long-chain compounds can be formed, wherein the self-assembled monolayer may exhibit (super)hydrophobicity, and at least partially covers the ZnO material (the hydrophilic layer), and wherein the area covered by the hydrophobic layer is called the detection area, which has a surface having an initial contact angle with water of more than or equal to about 120°, preferably, more than or equal to about 150°; thereby obtaining the (super) hydrophobic zinc sheet that can serve as the detection material of the present application. In the embodiment, in case that the ZnO layer (ZnO materials) of the resultant material is completely immersed into the solution, a hydrophobic layer that completely covers the hydrophilic layer can form. In case that the ZnO layer (ZnO materials) of the resultant material is partially immersed into the solution, a hydrophobic layer that partially covers the hydrophilic layer can form.

In another embodiment, a mask may also be provided on the surface of the resultant material before immersing the ZnO layer into a solution of one or more the long-chain compounds so as to form one or more areas on the ZnO layer (the hydrophilic layer) that are not covered by the mask; then immersing the ZnO layer into a solution of one or more the long-chain compounds is carried out, so that the hydrophobic layer will not form on the portion not covered by the mask, but form on the one or more areas that are not covered by the mask, thereby forming one or more of the detection areas.

In one embodiment, n-dodecyl thiol (DCT) is used as the long-chain compound, thus the superhydrophobic zinc sheet DCT-ZnO—Zn can be obtained. In another embodiment, n-octadecyl thiol (ODT) is used as the long-chain compound, thus the superhydrophobic zinc sheet ODT-ZnO—Zn can be obtained.

In one embodiment, a metal zinc rod can be used to prepare a (super)hydrophobic zinc rod by employing the same way as the above preparation of (super)hydrophobic zinc sheet.

Preferably, the detection material of the present application is selected from the (super)hydrophobic zinc sheet and the (super)hydrophobic zinc rod of the present application.

As mentioned above, a person skilled in the art can select an appropriate way and conditions to prepare the detection material of the present application if necessary.

Contacting the Detection Area of the Detection Material with the Aqueous Solution Sample FIG. 1 illustrates the mechanism of detecting Pb(II) or other types of heavy metal ions by using superhydrophobic zinc sheet (such as DCT-ZnO—Zn). The superhydrophobic DCT-ZnO—Zn is immersed in aqueous solution and maintained for a certain time (such as about 60 minutes). As illustrated in FIG. 1, if there is Pb(II) or other heavy metal ions [M(n+), e.g., may be Cd(II), Hg(II), and the like] in the aqueous solution, because the interaction between the heavy metal ion and the —SH group is stronger than the interaction between ZnO and —SH group, the self-assembled monolayer of DCT will separate from the surface of ZnO—Zn and react with Pb(II) or other heavy metal ions M(n+), thereby the surface of the superhydrophobic zinc sheet will turn from superhydrophobic to hydrophilic. On the contrary, if there is no heavy metal ion in the aqueous solution (or the concentrations of heavy metal ions are very low, e.g., lower than the lowest detection limit), the surface will still remain superhydrophobic. Therefore, the heavy metal ions in water can be detected with the superhydrophobic DCT-ZnO—Zn based on this hydrophobicity-hydrophilicity change.

Therefore, when the detection area of the detection material of the present application is contacted with the aqueous solution sample, if there exists a certain amount of heavy metal ions in the aqueous solution sample, the hydrophobic layer of the detection area (formed from a long-chain compound selected from the group consisting of a long-chain thiol, a long-chain fatty acid and combinations thereof) will have a hydrophobicity-hydrophilicity change. By detecting this hydrophobicity-hydrophilicity, it can be decided whether there exist heavy metal ions in the aqueous solution sample.

In one embodiment, the contact between the detection area of the detection material and the aqueous solution sample is carried out by immersing the detection area of the detection material into the aqueous solution sample. In one embodiment, the contact duration between the hydrophobic material and the aqueous solution sample is about 1 minute to about 5 hours. In another embodiment, the contact duration between the hydrophobic material and the aqueous solution sample is about 5 minutes to about 3 hours.

In one embodiment, the method of the application may further include adding solubilizer into the aqueous solution sample before or during the contacting of the detection area of the detection material with the aqueous solution sample; and/or, treating the detection material by applying an electric potential thereto during the contacting of the detection area of the detection material with the aqueous solution sample; this may shorten the detection duration and reduce the lowest detection limit, thus increasing the sensitivity of the detection.

In one embodiment, the method of the application may further include adding solubilizer into the aqueous solution sample before or during the contacting of the detection area of the detection material with the aqueous solution sample. The solubilizer may be added into the aqueous solution sample before the detection area of the detection material is contacted with the aqueous solution sample. Alternatively, solubilizer may be added into the aqueous solution sample during the contact between the detection area of the detection material and the aqueous solution sample.

In one embodiment, a water-soluble solubilizer includes, e.g., a water-soluble alcohol, such as $C_1$-$C_4$ aliphatic alcohol, such as methanol, ethanol, propanol, and the like. The water-soluble solubilizer may be used individually, or in combination. Without being bound by theory, it is believed that the addition of the water-soluble solubilizer into the aqueous solution sample may significantly increase the chance that the heavy metal ions encounter with the —SH group or —OH group of the long-chain compound from which the hydrophobic layer of the detection area is formed (selected from a long-chain thiol, a long-chain fatty acid and combinations thereof), thereby increasing the response rate and increasing the sensitivity of the detection. The variety and the amount of addition of the water-soluble solubilizer shall be insufficient to cause the hydrophobicity-hydrophilicity change of the surface of the detection area of the detection material. In one embodiment, the amount of the addition of the water-soluble solubilizer is less than or equal to about 10%, preferably about 1%~8%, and more preferably about 2%~6%, relative to the volume of the aqueous solution sample.

In another embodiment, the method of the present application may further include an electric treatment by applying an electric potential to the detection material during the contact between the detection area of the detection material with the aqueous solution sample, thereby shortening the duration of detection, reducing the lowest detection limit and increasing detection rate. In this embodiment, the detection material used should be conductive. In one embodiment, by carrying out an electric treatment on the detection material by applying a negative electric potential, the lowest detection limit may be reduced and the duration of detection may be shortened. While not wishing to be bound by any theory, it is believed that carrying out an electric treatment on the detection material by applying a negative electric potential may cause the surface of the detection area of the detection material to accumulate negative charges, thereby attracting and accumulating positively-charged heavy metal ions around the detection area, and can accelerate the interaction between the heavy metal ions and the long-chain compound from which the hydrophobic layer of the detection area is formed (selected from the group consisting of a long-chain thiol, a long-chain fatty acid and combinations thereof), thereby accelerating the hydrophobicity-hydrophilicity change of the surface of detection area, increasing the detection rate, and also further increasing the sensitivity of the detection. The level of the electric potential applied to the detection and the duration of the electric treatment may be selected if necessary. In one embodiment, an electric potential of −0.5~−20V, especially −1 to −15V, and more preferably −2~−8V may be applied to the detection material. In one embodiment, the duration of the electric treatment may be 1~40 minutes, preferably 3~30 minutes, and preferably 5~20 minutes.

In one embodiment, when an electric potential is applied to the detection material for the electric treatment, the portion of the detection material that contacts with the aqueous solution sample is preferably mostly (more preferably completely) covered by the hydrophobic layer to avoid the occurrence of reduction, even electrolysis of water when the metal oxide (e.g., ZnO) that is not covered by the hydrophobic layer contacts with the aqueous solution.

In another embodiment, the method of the present application may further include adding a solubilizer into the aqueous solution sample before and/or during the contacting of the detection area of the detection material with the aqueous solution sample. Moreover, during the contacting of the detection area of the detection material with the aqueous solution sample, the detection material is subjected to an electric potential for an electric treatment, thereby further shortening the duration of detection, reducing the lowest detection limit and increase the detection rate. As mentioned above, in this embodiment, the detection material is conductive. Examples of the water-soluble solubilizer include, but are not limited to, e.g., a water-soluble alcohol, such as $C_1$-$C_4$ aliphatic alcohol, such as methanol, ethanol, propanol, and the like. The water-soluble solubilizer may be used individually or in combination. In one embodiment, the amount of the addition of the water-soluble solubilizer is less than or equal to about 10%, preferably about 1%~8%, and more preferably about 2%~6%, relative to the volume of the aqueous solution sample. In another embodiment, an electric potential of −0.5~−20V, especially −1 to −15V, and more preferably −2~−8V, may be applied to the detection material. In another embodiment, the duration of the electric treatment may be 1~40 minutes, preferably 3~30 minutes, and preferably 5~20 minutes.

Determining Whether the Surface of the Detection Area of the Detection Material has a Hydrophobicity-Hydrophilicity Change; and Deciding Whether Heavy Metal Ions Exist in the Aqueous Solution Sample The method of the present application includes determining whether the surface of the detection area of the detection material has a hydrophobicity-hydrophilicity change after contacting with the aqueous solution sample; and deciding whether heavy metal ions exist in the aqueous solution sample according to the determination.

If it is determined that the detection area of the detection material has a hydrophobicity-hydrophilicity change after contacting with the aqueous solution sample, it can be decided that a certain amount of heavy metal ions exist in the aqueous solution sample. On the contrary, if it is determined that the detection area of the detection material does not have a hydrophobicity-hydrophilicity change after contacting with the aqueous solution sample, it can be decided that a certain amount of heavy metal ions do not exist in the aqueous solution sample, or the concentrations of the heavy metal ions are very low (e.g., lower than the lowest detection limit).

Usually, the hydrophobicity-hydrophilicity change of a material can be determined by physical or chemical methods.

These methods are carried out based on the physical or chemical changes caused by the hydrophobicity-hydrophilicity change of the material. For example, the hydrophobicity-hydrophilicity change may be determined by measuring or observing the change in contact angle with water.

In one embodiment, when the detection material has a contact angle between the surface of the detection area thereof and water is reduced by at least about 20°, e.g., at least about 25°, especially at least about 30° after contacting with the aqueous solution sample, compared with the initial contact angle of the surface of the detection area of the detection material with water, it may be determined that a hydrophobicity-hydrophilicity change occurs in the detection area of the detection material. In another embodiment, when the detection area of the detection material becomes hydrophilic after contacting with the aqueous solution sample, i.e., the contact angle with water less than about 90°, especially less than or equal to about 80°, more specifically less than or equal to 70°, it can also be determined that a hydrophobicity-hydrophilicity change occurs in the detection area of the detection material.

In another embodiment, for example, the following ways may be employed to determine whether a hydrophobicity-hydrophilicity change occurs in the detection area of the detection material:

(1) Determination by a colorant: the colorant used is one that does not have any heavy metal component, is water-soluble and can be adsorbed by a hydrophilic surface. A hydrophobic material will not adsorb the colorant after contacting and will not exhibit a color change. In case that the surface of the material changes from hydrophobic to hydrophilic, the colorant will be adsorbed to the surface of the material to cause coloration of the material. On the contrary, if no hydrophobicity-hydrophilicity change occurs, the surface of the material will not adsorb the colorant so as not to exhibit a color change.

(2) Measurement of resistance and/or current: the metal oxides (e.g., ZnO and the like) for the construction of the (super)hydrophobic material have the property of a humid-sensitive resistor, and thus the (super)hydrophobic material has a very high resistance when dry (hydrophobic). After contacting with the aqueous solution sample, if the surface of the material changes from hydrophobic to hydrophilic, it is readily wettable by water. When wetted (hydrophilic), its resistance is sharp reduced. Therefore, the hydrophobicity-hydrophilicity change on surface of the material may also be exhibited by a sharp change in resistance.

In one embodiment, a colorant is used to determine whether a hydrophobicity-hydrophilicity change occurs on the surface of the detection area of the detection material. Examples of the colorant is a water-soluble colorant, e.g., a water-soluble dye, examples including but not being limited to, aqueous ink such as red ink, blue ink, and the like, or other water soluble dye containing no heavy metal components. Very simple and direct determination is possible by employing this embodiment.

In one embodiment, the method of the present application may include adding a colorant into the aqueous solution sample before and/or during the contacting of the detection area of the detection material with the aqueous solution sample. After the detection area of the detection material has contacted the aqueous solution sample for a certain time, if the detection area of the detection material is able to adsorb the colorant and exhibit a color, it may be determined that a hydrophobicity-hydrophilicity change occurs on its surface, and a certain amount of heavy metal ions exist in the aqueous solution sample. Otherwise, it may be determined that no heavy metal ion exists in the aqueous solution sample (or the concentrations of the heavy metal ions are very low, e.g., lower than the lowest detection limit).

In another embodiment, the method of the present application may also include immersing the detection area of the detection material having contacted the aqueous solution sample, and carrying out determining whether the surface of the detection area of the detection material has a hydrophobicity-hydrophilicity change by observing whether the surface of the detection area exhibits a color change. If the detection area of the detection material is able to adsorb the colorant and exhibit a color, it may be determined that a hydrophobicity-hydrophilicity change occurs on its surface, and a certain amount of heavy metal ions exist in the aqueous solution sample. Otherwise, it may be determined that no heavy metal ion exists in the aqueous solution sample (or the concentrations of the heavy metal ions are very low, e.g., lower than the lowest detection limit).

The term "heavy metal ions" as used herein refers to ions of metal elements with a density higher than 4.5 g/cm$^3$. The method of the present application is suitable for the detection of almost all heavy metal ions, primarily including Zn(II), Cu(II), Cd(II), Pb(II), Ag(I), Hg(II) and Hg$_2$(II), in particular the common heavy metal ions that pose huge threats to human, e.g., Cd(II), Pb(II), Hg(II), and the like.

By using the method of the present application, the existence of non-heavy metal ions will not interfere with the detection of the heavy metal ions, so the method is very effective. As proved by the following examples, even if there are non-heavy metal ions such as K$^+$, Na$^+$, Mg$^{2+}$, Ca$^{2+}$, and the like, in the aqueous solution, by using the superhydrophilic zinc sheet, heavy metal ions such as one or more of Hg$^{2+}$, Hg$_2^{2+}$, Pb$^{2+}$, Cd$^{2+}$, Cu$^{2+}$ and Zn$^{2+}$ may be detected within a very brief time (such as 15 minutes) with a very high sensitivity of detection and without the need of any complicated pre-treatment. For example, by using the method of the present application, Hg$^{2+}$ (about 10$^{-7}$M or more), Hg$_2^{2+}$ (about 10$^{-7}$M or more), Pb$^{2+}$ (about 10$^{-6}$M or more), Cd$^{2+}$ (about 10$^{-6}$M or more), Cu$^{2+}$ (about 10$^{-5}$M or more), and Zn$^{2+}$ (about 10$^{-5}$M or more) may be detected; alternatively, these heavy metal ions may be simultaneously detected (total concentration about 10$^{-6}$M or more).

Device and Detection Kit for the Detection of Heavy Metal Ions in Aqueous Solution Another aspect of the application relates to a device for the detection of heavy metal ions in aqueous solution including a main body and a detection material, wherein the detection material includes a hydrophilic layer, which is at least partially covered by a hydrophobic layer formed from a long-chain compound selected from the group consisting of a long-chain thiol, a long-chain fatty acid and combinations thereof, and wherein a detection area is defined by an area covered by the hydrophobic layer, which has a surface having an initial contact angle with water of more than or equal to about 120°; wherein the detection area of the detection material may be exposed in the exterior of the main body for contacting the aqueous solution.

For example, the detection material may be directly arranged on the main body of the device so that the detection area of the detection material is exposed in the exterior of the main body for contacting the aqueous solution sample.

Alternatively, the detection material may also be placed in the interior of the main body of the device so that the detection area of the detection material may be moved from the interior to the exterior of the main body of the device for contacting the aqueous solution sample.

Furthermore, the device of the present application can be designed as a portable detection device that is convenient to carry. For example, in one embodiment, the portable detection device may include a housing with an opening. A passage that can host the detection material is placed inside the housing, and the detection material may move in the passage so that the detection area of the detection material may move outside the housing through the opening. The device may further include a moveable sliding block on which the detection material may be detachably fixated. The detection material can be moved along the passage by moving the sliding block so that the detection area of the detection material may extrude outside the housing through the opening. In one embodiment, the portable detection device may be provided as a pen to form a portable detection pen. The portable detection pen has a pen-shaped housing with the opening disposed at the end of the pen-shaped housing. The detection material is hosted inside the pen-shaped housing so that the detection area of the detection material may extrude outside the housing through the opening.

In one embodiment, the sliding block may be arranged on a guiding rail and move along it so as to move the detection material. The passage that hosts the detection material may be formed from the guiding rail and the housing.

In another embodiment, in order to preserve the detection material, the device further includes a sealing means covering the opening. During the preservation, the sealing means is used for the sealing of the opening. When the device is used for detection, the sealing means may be removed and the detection area of the detection material is moved outside the housing by moving the sliding block. By controlling the distance of the sliding block movement, the extrusion extent of the detection area of the detection material outside the housing is controlled.

In one embodiment, the sliding block may be placed to be conductive when an electric treatment is needed to accelerate the detection process. Furthermore, a stake of wire may be disposed on the conductive sliding block to facilitate the application of the electric potential so that by connecting the stake of wire with a power supply an electric potential may be applied to the detection material.

The various embodiments with respect to the detection material in "method for the detection of heavy metal ions in aqueous solution" section herein are also applicable to the device of the present application.

In one embodiment, the detection material used in the device includes a metal substrate and a hydrophilic layer on the substrate, which is at least partially covered by a hydrophobic layer, wherein the hydrophilic layer is formed from a metal oxide and the hydrophobic layer is formed from a long-chain compound selected from a long-chain thiol, a long-chain fatty acid and combinations thereof, and wherein an area covered by the hydrophobic layer is defined as a detection area which has a surface having an initial contact angle with water of more than or equal to about 120°, preferably, an initial contact angle with water of more than or equal to about 150°.

In another embodiment, the detection material used in the device is selected from the (super)hydrophobic zinc sheet, the (super)hydrophobic zinc rod and combinations thereof according to the present application. The detection area of the detection material of the device may be inserted into the colorant solution after contacting the aqueous solution sample for an in situ determination to facilitate the detection. The colorant may be a water-soluble colorant, including a water soluble dye such as red ink, blue ink, or the like.

In another aspect of the present application, the device of the present application may be assembled into a detection kit, which includes the device of the present application and a container filled with a colorant solution. The detection area of the detection material of the device may be inserted into the colorant solution after contacting the aqueous solution sample for an in situ determination to facilitate the detection. The colorant may be a water-soluble colorant, including a water soluble dye such as red ink, blue ink, and the like.

In another embodiment, the detection kit can further include a container filled with a water soluble solubilizer and/or electrolysis equipment. As mentioned above, the time of the detection may be shortened and the sensitivity of the detection may be increased by using the water-soluble solubilizer and/or carrying out an electric treatment. The water-soluble solubilizer includes a water-soluble alcohol such as a $C_1$-$C_4$ aliphatic alcohol, preferably ethanol, and the like. By using this electrolysis equipment, the electric treatment may be carried out during the detection. The electrolysis equipment may include an electrolyte tank, a reference electrode, a counter electrode and a power supply.

The detection kit may be used for detection as follows: the aqueous solution sample is taken and poured into the electrolyte tank of the electrolysis equipment. Optionally, an amount of the water soluble solubilizer is added. The detection area of the detection material is immersed into the aqueous solution sample. Then the electrolysis equipment is connected so that a negative electric potential is applied to the detection material for the electric treatment. Subsequently, the detection material is taken out. The detection area of the detection material is immersed into a colorant solution after contacting the aqueous solution sample so as to determine whether the heavy metal ions exist in the aqueous solution sample by determining whether the detection area adsorbs the colorant solution (i.e., whether it exhibits a color change).

As mentioned above, the device and the detection kit of the present application may in situ detect the heavy metal ions in water system, especially those including ions of cadmium (Cd), lead (Pb), mercury (Hg), copper (Cu) and zinc (Zn), particularly the common ions of cadmium (Cd), lead (Pd), mercury (Hg), and the like, those are toxic to human being, with a low cost. Moreover, the device and the detection kit of the present application are simple to use and not limited by the environment conditions.

Example

Example 1

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

Figure 2:
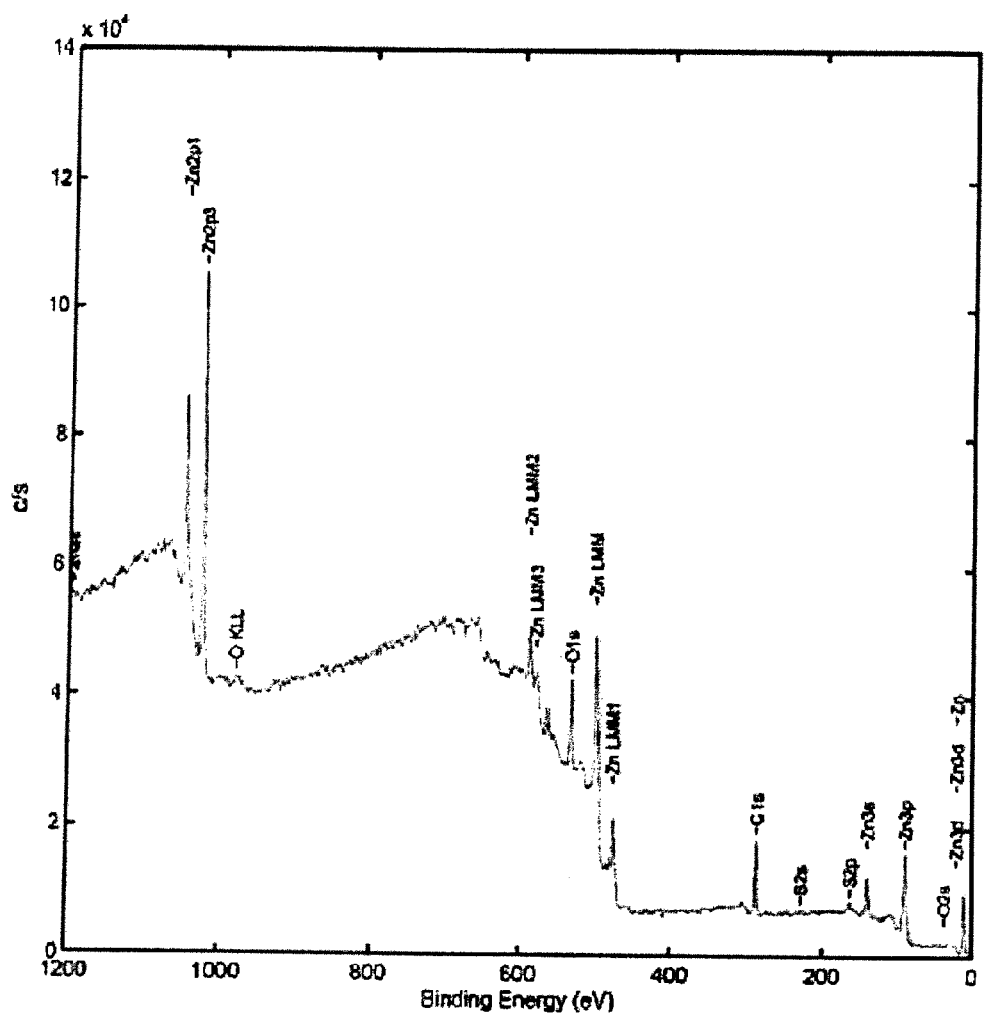
FIG. 2 is the SEM image of ZNO nanorod in the zinc sheet and XPS spectrum of DCT-ZnO—Zn.

During the aforementioned preparation, the resultant material could be analyzed by employing a scanning electronic microscope (SEM) and a X-ray photoelectron spectroscopy (XPS). FIG. 2 illustrates the XPS spectrum of superhydrophobic zinc sheet and the SEM image of the ZnO nanolayer formed after oxidation of the zinc sheet in the 8% N,N-dimethylacetamide-water solution. The results showed that the oxidized Zn surface showed nanorod array of hexagonal ZnO crystals that were highly oriented and tightly packed.

After the self-assembly of n-dodecyl thiol (DCT), it could be observed from the XPS spectrum that the surface of the zinc sheet was composed of Zn, O, C and S elements, which confirmed that DCT has successfully self-assembled on the surface of ZnO—Zn.

Water drops were dropped onto the following selected zinc sheets: (a) a pure zinc sheet (Zn); (b) an oxidized zinc sheet (ZnO—Zn); and (c) a ZnO—Zn self-assembled with DCT (DCT-ZnO—Zn).

In the meantime, at room temperature, three superhydrophobic zinc sheet DCT-ZnO—Zn were individually immersed in the following solution for 60 minutes or more, and then taken out, and water drops were dropped onto their surface to observe the appearance of the water drop: (d) pure water; (e) $5\times10^{-5}$ M KCl aqueous solution; and (f) $1\times10^{-5}$ M $Pb(NO_3)_2$ aqueous solution.

FIGS. 3a-f are images illustrating water drops on different zinc sheets. (a) is an image of a water drop on a pure zinc sheet (Zn); (b) is an image of a water drop on an oxidized zinc sheet (ZnO—Zn); (c) is an image of a water drop on ZnO—Zn self-assembled with DCT (DCT-ZnO—Zn); (d) is an image of a water drop on DCT-ZnO—Zn treated with pure water for 60 minutes or more; (e) is an image of a water drop on DCT-ZnO—Zn treated with $5\times10^{-5}$ M KCl aqueous solution for 60 minutes or more; and (f) is an image of a water drop on DCT-ZnO—Zn treated with $1\times10^{-5}$ M $Pb(NO_3)_2$ aqueous solution for 60 minutes or more.

Figure 3:
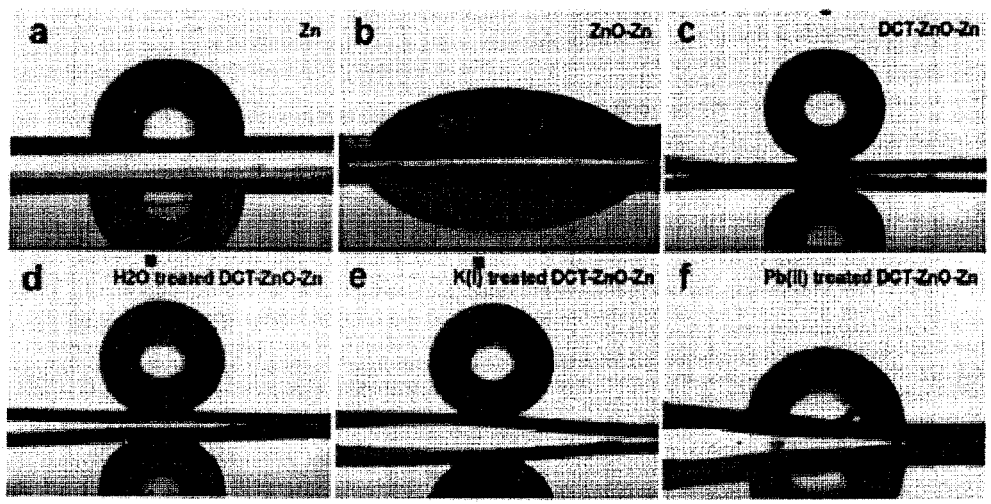
FIG. 3 is a photo of droplets on the surface of a zinc sheet, an oxidized zinc sheet, an oxidized and superhydrophobic zinc sheet and a superhydrophobic zinc sheet treated with solution of various metal ions. (a) Pure zinc sheet; (b) oxidized zinc sheet, ZnO—Zn; (c) ZnO—Zn self-assembled with DCT; (d) DCT-ZnO—Zn treated with pure water for 60 minutes or more; (e) DCT-ZnO—Zn treated with $5 \times 10^{-5}$ M KCl aqueous solution for 60 minutes or more; and (f) DCT-ZnO—Zn treated with $1 \times 10^{-5}$ M $Pb(NO_3)_2$ aqueous solution for 60 minutes or more.

From FIGS. 3a-c, after oxidation, ZnO—Zn has a more hydrophilic surface than the pure zinc sheet, while the surface of ZnO modified with the long-chain thiol DCT or ODT exhibits superhydrophobicity. It has a contact angle CA with water of >150°, indicating that a superhydrophobic zinc sheet is obtained.

FIGS. 3d-f are images illustrating water drops on superhydrophobic zinc sheets after different treatments. The images of water drops on these treated DCT-ZnO—Zn clearly show that only the Pb(II) treated DCT-ZnO—Zn has an obvious surface change with a contact angle of about 70°, while DCT-ZnO—Zn treated with pure water and K(I) still retain their superhydrophobicity. This indicates that a portion of DCT has already detached from the ZnO—Zn via Pb(II), but the DCT cannot be removed by K(I) or pure water. That is to say, among the three of pure water, K(I) and the heavy metal ion Pb(II), only the heavy metal ion Pb(II) can cause a hydrophobicity-hydrophilicity change in the surface of the superhydrophobic zinc sheet. Therefore, the hydrophobicity-hydrophilicity change in the surface of DCT-ZnO—Zn can be used to detect the heavy metal ions in water.

XPS was also employed to analyze the DCT-ZnO—Zn before and after the treatment with $1\times10^{-5}$ M $Pb(NO_3)_2$ aqueous solution.

Figure 4:
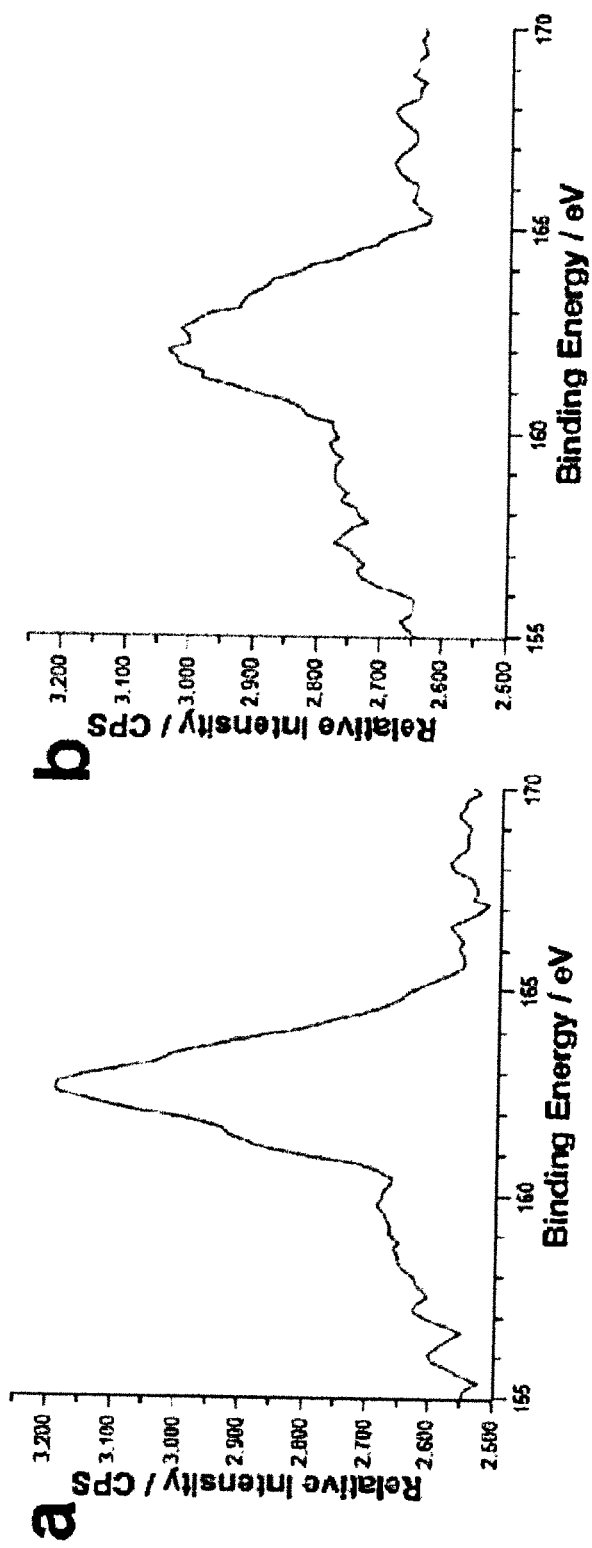
FIG. 4 shows images of the S region of the XPS spectrum of DCT-ZnO—Zn. (a) An image of the S region of the XPS spectrum of DCT-ZnO—Zn not treated with metal ions; and (b) an image of the S region of the XPS spectrum of DCT-ZnO—Zn treated with Pb(II).

FIG. 4 illustrates the change in relative intensity of S element in DCT-ZnO—Zn before and after the Pb(II) treatment, wherein FIG. 4(a) is the spectrum of S element in the surface XPS spectrum of DCT-ZnO—Zn before the Pb(II) treatment, and FIG. 4(b) is the spectrum of S element in the surface XPS spectrum of DCT-ZnO—Zn after the Pb(II) treatment. From the figure, it is obvious that after Pb(II) treatment, the relative intensity of S element in the XPS spectrum is reduced, which further proves that a portion of DCT escapes when the superhydrophobic zinc sheet encounters the Pb(II) in water. The results indicate that the hydrophobicity-hydrophilicity change in the surface of the superhydrophobic zinc sheet is caused by the release of the long-chain thiol (DCT) from its surface.

Example 2

As mentioned above, the addition of an organic compound into the aqueous solution sample, and/or electric treatment, may shorten the duration of detection, reduce the lowest detection limit and increase the detection rate.

In the present example, the detection of heavy metal ions in aqueous solution using the superhydrophobic zinc sheet DCT-ZnO—Zn prepared in Example 1 under the conditions of ethanol (EtOH) addition and/or electric treatment was examined.

In the present example, 5 volume % (by the volume of the aqueous solution sample) of EtOH was added into the aqueous solution sample as a water-soluble solubilizer. The electric treatment was carried out as follows: a negative electric potential (−3V) is applied to the superhydrophobic zinc sheet with the superhydrophobic zinc sheet serving as a working electrode, Pt wire serving as a counter electrode and Ag/AgCl electrode serving as a reference electrode.

In addition, for a better observation, after various treatments, the treated superhydrophobic zinc sheet was immersed into a read colorant (red ink) to facilitate the determination. In case that the superhydrophobic zinc sheet exhibited superhydrophobicity, the red colorant would not be absorbed onto the superhydrophobic zinc sheet so as no color change was exhibited. On the contrary, in case that a hydrophobicity-hydrophilicity change occurred in the superhydrophobic zinc sheet so that it exhibited a certain degree of hydrophilicity, the red colorant would be absorbed onto it so as to exhibit a color change. The greater the hydrophobicity-hydrophilicity change, the more obvious was the change of the exhibited color. Whether a hydrophobicity-hydrophilicity change occurred in the superhydrophobic zinc sheet can be determined by observing the color change of the superhydrophobic zinc sheet.

Figure 5:
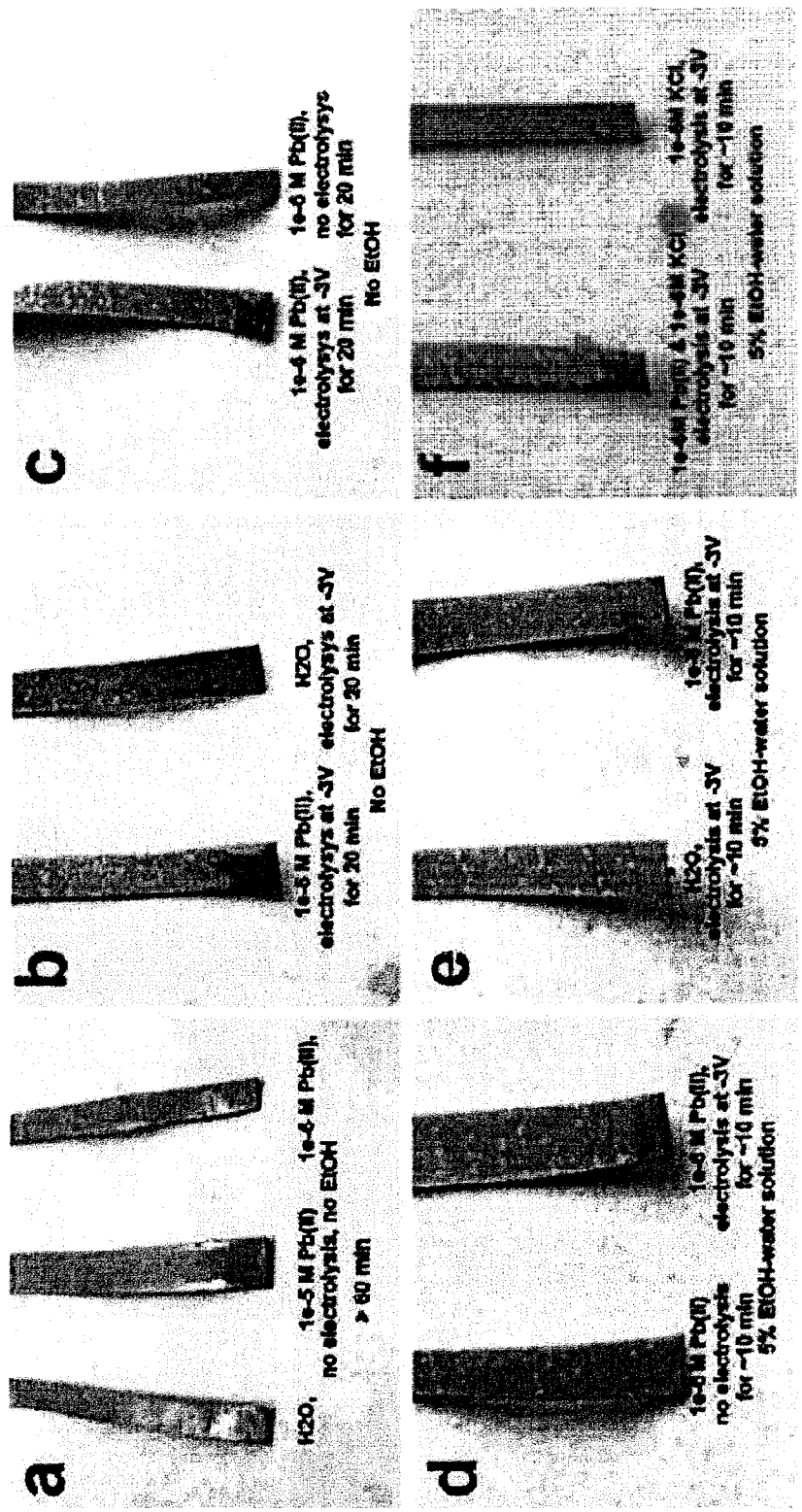
FIG. 5 illustrates the results of detection of Pb(II) in water under different assay conditions by the color change of superhydrophobic zinc sheet with the aid of proper colorants.

FIG. 5 illustrates the results of the detection of Pb(II) in water by the color change of the superhydrophobic zinc sheet under different assay conditions with the aid of red ink (aqueous solution).

FIG. 5(a) illustrates the results of immersing the superhydrophobic zinc sheet into pure water, $1\times10^{-5}$M $Pb(NO_3)_2$ aqueous solution and $1\times10^{-6}$M $Pb(NO_3)_2$ aqueous solution without EtOH addition and without electric treatment, and treating for 60 minutes or more. The results showed that only the superhydrophobic zinc sheet treated with $1\times10^{-5}$M $Pb(NO_3)_2$ aqueous solution had a shallow color change, while the superhydrophobic zinc sheet treated with pure water and $1\times10^{-6}$M $Pb(NO_3)_2$ aqueous solution did not exhibit any color change.

FIG. 5(b) describes the results of immersing the superhydrophobic zinc sheets individually in $1\times10^{-6}$M $Pb(NO_3)_2$ aqueous solution and pure water under the conditions that EtOH was not added but the electric treatment was conducted at −3V for 20 minutes. The results showed that under the electric treatment, very significant color change occurred in the superhydrophobic zinc sheet treated with $1\times10^{-6}$M $Pb(NO_3)_2$ aqueous solution within only 20 minutes, whereas no color change occurred in the superhydrophobic zinc sheet treated by water.

FIG. 5(c) describes the results of immersing superhydrophobic zinc sheets into $1\times10^{-6}$M $Pb(NO_3)_2$ aqueous solution with or without the electric treatment at −3V for 24 minutes, respectively. The results showed that a significant color change occurred in the superhydrophobic zinc sheet with the electric treatment, whereas no color change was shown for the superhydrophobic zinc sheet without the electric treatment.

The results of FIGS. 5(a)~5(c) confirm that the electric treatment without the addition of the water-soluble solubilizer can not only greatly shorten the duration of detection, but also reduce the lowest detection limit of the heavy metal ion (Pb(II)) (e.g., by at least one order of magnitude).

FIG. 5(d) describes the results of immersing the superhydrophobic zinc sheets into $1\times10^{-6}$ M $Pb(NO_3)_2$ aqueous solution with the addition of 5 volume % EtOH-water solution and with or without the electric treatment at $-3V$ for 10 minutes, respectively. The results showed that with the addition of EtOH, a very significant color change occurred in the superhydrophobic zinc sheet subjected to the electric treatment within only 10 minutes, whereas no color change occurred in the superhydrophobic zinc sheet treated without being subjected to the electric treatment.

FIG. 5(e) describes the results of immersing the superhydrophobic zinc sheets into $1\times10^{-6}$ M $Pb(NO_3)_2$ aqueous solution and water, respectively, with the addition of 5 volume % EtOH-water solution and with the electric treatment at $-3V$ for 10 minutes. The results showed that a very significant color change occurred in the superhydrophobic zinc sheet treated with $1\times10^{-6}$ M $Pb(NO_3)_2$ aqueous solution, whereas no color change occurred in the superhydrophobic zinc sheet treated by water.

The results of FIG. 5(d)~5(e) confirm that with both the addition of a water-soluble solubilizer (e.g., EtOH) and the electric treatment, the lowest detection limit can be reduced while the duration of detection can be further shortened.

FIG. 5(f) describes the results of immersing the superhydrophobic zinc sheets into $1\times10^{-6}$ M $Pb(NO_3)_2+1\times10^{-6}$ M KCl aqueous solution and $1\times10^{-6}$ M KCl aqueous solution, respectively, with the addition of 5 volume % EtOH-water solution and with electric treatment at $-3V$ for 10 minutes. The results showed that a significant color change occurred in the superhydrophobic zinc sheet treated with $1\times10^{-6}$ M $Pb(NO_3)_2+1\times10^{-6}$ M KCl aqueous solution, whereas no color change occurred in the superhydrophobic zinc sheet treated with $1\times10^{-6}$ M KCl aqueous solution. This result also confirmed that the presence of K(I) would not interfere with the detection of Pb(II).

The results of FIG. 5(a)~(f) also illustrated that using a water-soluble solubilizer and/or applying an electric potential to the detection material for an electric treatment in the method of the present application, the lowest detection limit can be significantly reduced (e.g., by at least one order of magnitude) while the duration of detection can be significantly shortened (e.g., a significant hydrophobicity-hydrophilicity change may occur at about 10 minutes). In addition, in case that the superhydrophobic zinc sheet is immersed in pure water or non-heavy metal ion solution, even with the addition of 5% EtOH and the electric treatment, no hydrophobicity-hydrophilicity change in the superhydrophobic zinc sheet may be effected, indicating the presence of non-heavy metal ion will not interfere with the method for the detection of heavy metal ions according to the present application.

Example 3

Detection of Zn(II), Cu(II) or Pb(II) in Aqueous Solution

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL of $MgSO_4(1\times10^{-5}M)$ aqueous solution, $CaCl_2(1\times10^{-5}M)$ aqueous solution, $ZnCl_2(1\times10^{-5}M)$ aqueous solution, $Cu(NO_3)_2(1\times10^{-5}M)$ aqueous solution or $Pb(NO_3)_2(1\times10^{-6}M)$ that contains 5% EtOH in each case, respectively, with the superhydrophobic zinc sheets serving as a working electrode, Pt wire serving as a counter electrode and Ag/AgCl electrode serving as a reference electrode. An electric potential of $-3V$ was applied to the superhydrophobic zinc sheets for 10 minutes for the electric treatment, and then immersed into red ink aqueous solution to observe the change in their surfaces.

Figure 6:
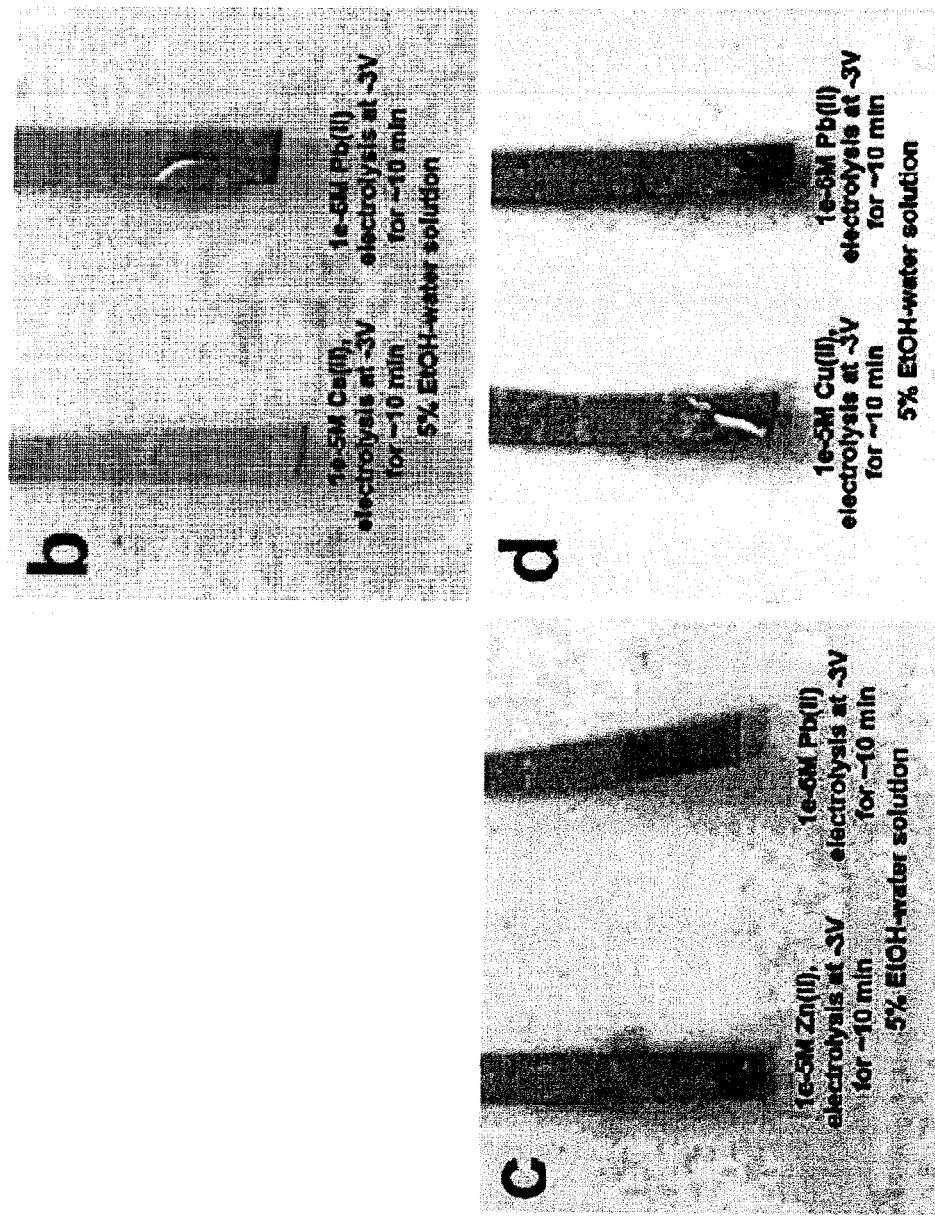
FIG. 6 illustrates that the hydrophobicity-hydrophilicity change on the surface of the superhydrophobic zinc sheet depends on the type of the metal ions. The response capacity of the superhydrophobic zinc sheet to Pb(II), Cu(II), Zn(II), Ca(II) and Mg(II) is in the following order: Pb(II)>Cu(II), Zn(II)>Ca(II), Mg(II).

FIG. 6 shows the images of the superhydrophobic zinc sheets prepared in the present example after electric treatment in the aqueous solution of $1\times10^{-6}$ M Pb(II), $1\times10^{-5}$ M Mg(II), $1\times10^{-5}$ M Ca(II), $1\times10^{-5}$ M Zn(II) and $1\times10^{-5}$ M Cu(II). Among them, FIG. 6a illustrates the images of the superhydrophobic zinc sheets after electric treatment in the aqueous solution of $1\times10^{-6}$ M Pb(II) and $1\times10^{-5}$ M Mg(II), respectively; FIG. 6b illustrates the images of the superhydrophobic zinc sheets after electric treatment in the aqueous solution of $1\times10^{-5}$ M Ca(II) and $1\times10^{-6}$ M Pb(II), respectively; FIG. 6c illustrates the images of the superhydrophobic zinc sheets after electric treatment in the aqueous solution of $1\times10^{-5}$ M Zn(II) and $1\times10^{-6}$ M Pb(II), respectively; and FIG. 6d illustrates the images of the superhydrophobic zinc sheets after electric treatment in the aqueous solution of $1\times10^{-5}$ M Cu(II) and $1\times10^{-6}$ M Pb(II), respectively.

From FIGS. 6(a)~6(d), it is obvious that the superhydrophobic zinc sheets exhibited significant color changes after being treated with the aqueous solution of $1\times10^{-6}$ M Pb(II), $1\times10^{-5}$ M Zn(II), or $1\times10^{-5}$ M Cu(II), indicating the occurrence of hydrophobicity-hydrophilicity change; whereas the superhydrophobic zinc sheets exhibited almost no color change after being treated with the aqueous solution of $1\times10^{-5}$ M Mg(II)+$1\times10^{-5}$ M Ca(II). This means that the detection material of the present application (the superhydrophobic zinc sheet) can be used to detect heavy metal ions such as Pb(II), Zn(II) and Cu(II) with the lowest detection limits at least down to $1\times10^{-6}$ M Pb(II), $1\times10^{-5}$ M Zn(II), and $1\times10^{-5}$ M Cu(II), respectively; whereas the non-heavy metal ions Ca(II) or Mg(II) cannot change the surface hydrophobicity of the detection area of the detection material of the present application, thus will not interfere with the method of the present application.

Example 4

Detection of Pb(II) in Aqueous Solution in the Presence of Mg(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $MgSO_4(5\times10^{-5}M)$ aqueous solution containing 5% EtOH as well as 20 mL aqueous solution of $Pb(NO_3)_2(1\times10^{-6}M)$ and $MgSO_4(5\times10^{-5}M)$ that contains 5% EtOH, with the superhydrophobic zinc sheets serving as a working electrode, Pt wire serving as a counter electrode and Ag/AgCl electrode serving as a reference electrode for the detection.

An electric potential of −3V was applied to the superhydrophobic zinc sheets for 10 minutes for the electric treatment, and then immersed into red ink aqueous solution to observe the change in their surfaces.

Figure 7:
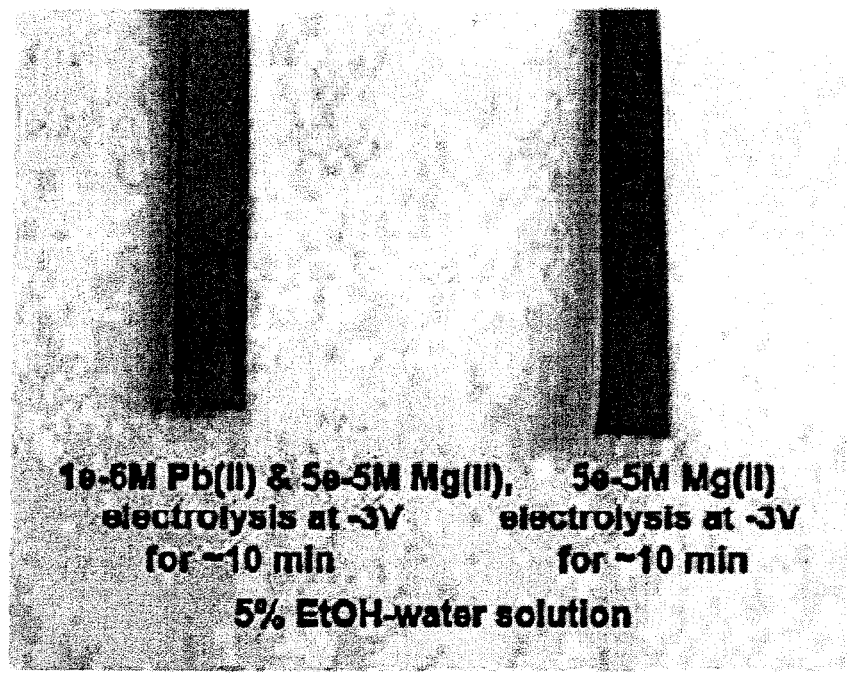
FIG. 7 is a diagram illustrating the results of detecting Pb(II) with the superhydrophobic zinc sheet in the presence of Mg(II).

FIG. 7 shows the images of the superhydrophobic zinc sheets after electric treatment in the $5\times10^{-5}$ M Mg(II) aqueous solution and the aqueous solution containing $5\times10^{-5}$ M Mg(II)+$1\times10^{-6}$ M Pb(II). Obviously, after being treated with aqueous solution of Pb(II)+Mg(II), a color change occurred in the superhydrophobic zinc sheet, indicating the occurrence of a hydrophobicity-hydrophilicity change; whereas the superhydrophobic zinc sheet treated with the aqueous solution of Mg(II) did not exhibit any color change, indicating that Mg(II) could not change the surface hydrophobicity of the superhydrophobic zinc sheet. This means that the presence of Mg (II) will not interfere with the detection of Pb(II) in the method of the present application. Pb(II) can be detected in the presence of Mg(II) with the lowest detection limit at least down to $1\times10^{-6}$ M Pb(II).

Example 5

Detection of Cd(II) in Aqueous Solution in the Presence of Mg(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $MgSO_4$($5\times10^{-5}$M) aqueous solution containing 5% EtOH as well as 20 mL aqueous solution of $CdCl_2$($1\times10^{-6}$M) and $MgSO_4$($5\times10^{-5}$M) containing 5% EtOH, with the superhydrophobic zinc sheets serving as a working electrode, Pt wire serving as a counter electrode and Ag/AgCl electrode serving as a reference electrode for the detection. An electric potential of −3V was applied to the superhydrophobic zinc sheets for 10 minutes for the electric treatment, and then immersed into red ink aqueous solution to observe the change in their surfaces.

Figure 8:
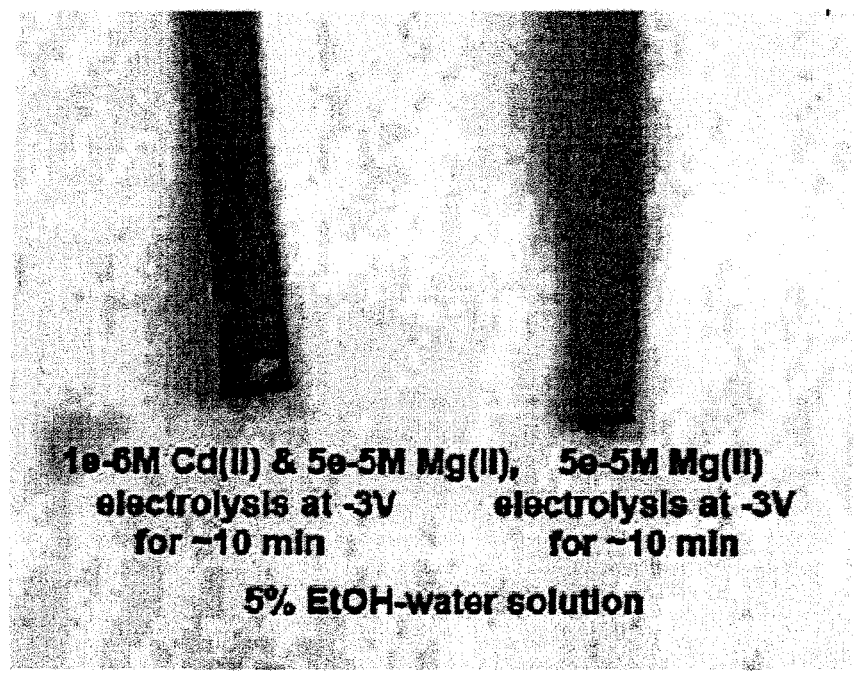
FIG. 8 is a diagram illustrating the results of detecting Cd(II) with the superhydrophobic zinc sheet in the presence of Mg(II).

FIG. 8 shows the images of the superhydrophobic zinc sheets after electric treatment in the $5\times10^{-5}$ M Mg(II) aqueous solution and the aqueous solution containing $5\times10^{-5}$ M Mg(II)+$1\times10^{-6}$ M Cd(II). Obviously, after being treated with aqueous solution of Cd(II)+Mg(II), a color change occurred in the superhydrophobic zinc sheet, indicating the occurrence of a hydrophobicity-hydrophilicity change; whereas the superhydrophobic zinc sheet treated with the aqueous solution of Mg(II) did not exhibit any color change, indicating that Mg(II) could not change the surface hydrophobicity of the superhydrophobic zinc sheet. This means that the presence of Mg (II) will not interfere with the detection of Cd(II) in the method of the present application. Cd(II) can be detected in the presence of Mg(II) with the lowest detection limit at least down to $1\times10^{-6}$ M Cd(II).

Example 6

Detection of Hg(II) in Aqueous Solution in the Presence of Mg(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $MgSO_4$($5\times10^{-5}$M) aqueous solution containing 5% EtOH as well as 20 mL aqueous solution of $HgSO_4$ ($1\times10^{-7}$M) and $MgSO_4$($5\times10^{-5}$M) containing 5% EtOH, with the superhydrophobic zinc sheets serving as a working electrode, Pt wire serving as a counter electrode and Ag/AgCl electrode serving as a reference electrode for the detection. An electric potential of −3V was applied to the superhydrophobic zinc sheets for 10 minutes for the electric treatment, and then immersed into red ink aqueous solution to observe the change in their surfaces.

Figure 9:
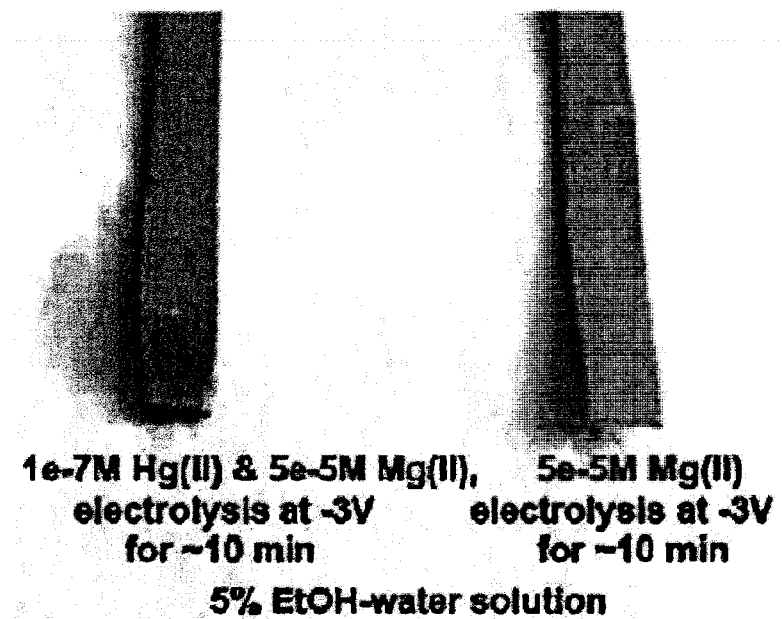
FIG. 9 is a diagram illustrating the results of detecting Hg(II) with the superhydrophobic zinc sheet in the presence of Mg(II).

FIG. 9 shows the images of the superhydrophobic zinc sheets after an electric treatment in the $5\times10^{-5}$ M Mg(II) aqueous solution and the aqueous solution containing $5\times10^{-5}$ M Mg(II)+$1\times10^{-7}$ M Hg(II). Obviously, after being treated with aqueous solution of Hg(II)+Mg(II), a significant color change occurred in the superhydrophobic zinc sheet, indicating the occurrence of a large hydrophobicity-hydrophilicity change; whereas the superhydrophobic zinc sheet treated with the aqueous solution of Mg(II) did not exhibit any color change, indicating that Mg(II) could not change the surface hydrophobicity of the superhydrophobic zinc sheet. This means that the presence of Mg (II) will not interfere with the detection of Hg(II) in the method of the present application. Hg(II) can be detected in the presence of Mg(II) with the lowest detection limit at least down to $1\times10^{-7}$ M Hg(II).

Example 7

Detection of Hg2(II) in Aqueous Solution in the Presence of Mg(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $MgSO_4$($5\times10^{-5}$M) aqueous solution containing 5% EtOH as well as 20 mL aqueous solution of $Hg_2Cl_2$($1\times10^{-7}$M) and $MgSO_4$($5\times10^{-5}$M) containing 5% EtOH, with the superhydrophobic zinc sheets serving as a working electrode, Pt wire serving as a counter electrode and Ag/AgCl electrode serving as a reference electrode for the detection. An electric potential of −3V was applied to the superhydrophobic zinc sheets for 10 minutes for the electric treatment, and then immersed into red ink aqueous solution to observe the change in their surfaces.

Figure 10:
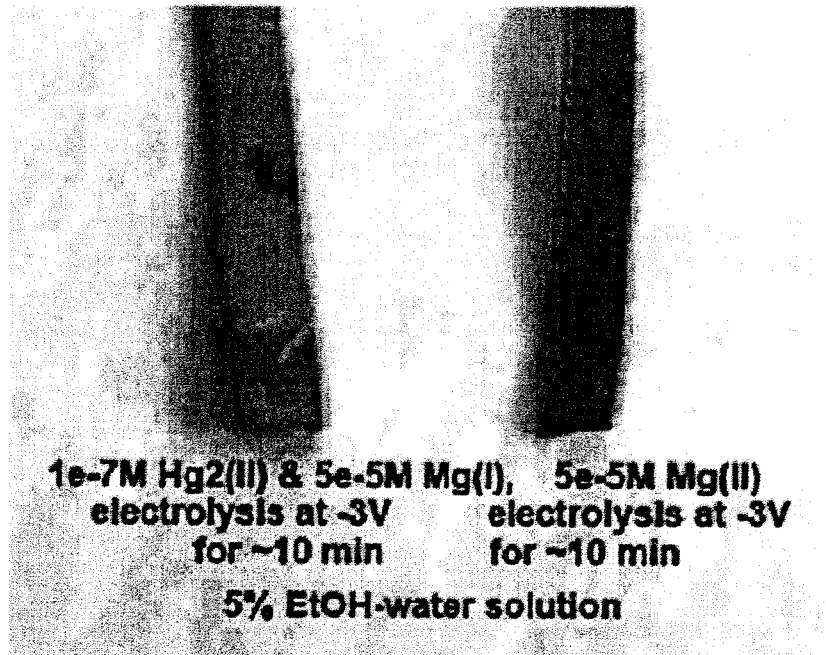
FIG. 10 is a diagram illustrating the results of detecting $Hg_2$(II) with the superhydrophobic zinc sheet in the presence of Mg(II).

FIG. 10 shows the images of the superhydrophobic zinc sheets after an electric treatment in the $5\times10^{-5}$ M Mg(II) aqueous solution and the aqueous solution containing $5\times10^{-5}$ M Mg(II)+$1\times10^{-7}$ M $Hg_2$(II). Obviously, after being treated with aqueous solution of $Hg_2$(II)+Mg(II), a significant color change occurred in the superhydrophobic zinc sheet, indicating the occurrence of a large hydrophobicity-hydrophilicity change; whereas the superhydrophobic zinc sheet treated with the aqueous solution of Mg(II) did not exhibit any color change, indicating that Mg(II) could not change the surface hydrophobicity of the superhydrophobic zinc sheet. This means that the presence of Mg (II) will not interfere with the detection of $Hg_2$(II) in the method of the present application. $Hg_2$(II) can be detected in the presence of Mg(II) with the lowest detection limit at least down to $1\times10^{-7}$ M $Hg_2$ (II).

Example 8

Simultaneous Detection of Pb(II) and Cd(II) in Aqueous Solution in the Presence of Mg(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $MgSO_4$($5\times10^{-5}$M) aqueous solution containing 5% EtOH as well as 20 mL aqueous solution of $Pb(NO_3)_2$($8\times10^{-7}$M), $CdCl_2$($4\times10^{-7}$M) and $MgSO_4$($5\times10^{-5}$M) containing 5% EtOH, with the superhydrophobic zinc sheets serving as a working electrode, Pt wire serving as a counter electrode and Ag/AgCl electrode serving as a reference electrode for the detection. An electric potential of −3V was applied to the superhydrophobic zinc sheets for 10 minutes for the electric treatment, and then immersed into red ink aqueous solution to observe the change in their surfaces.

Figure 11:
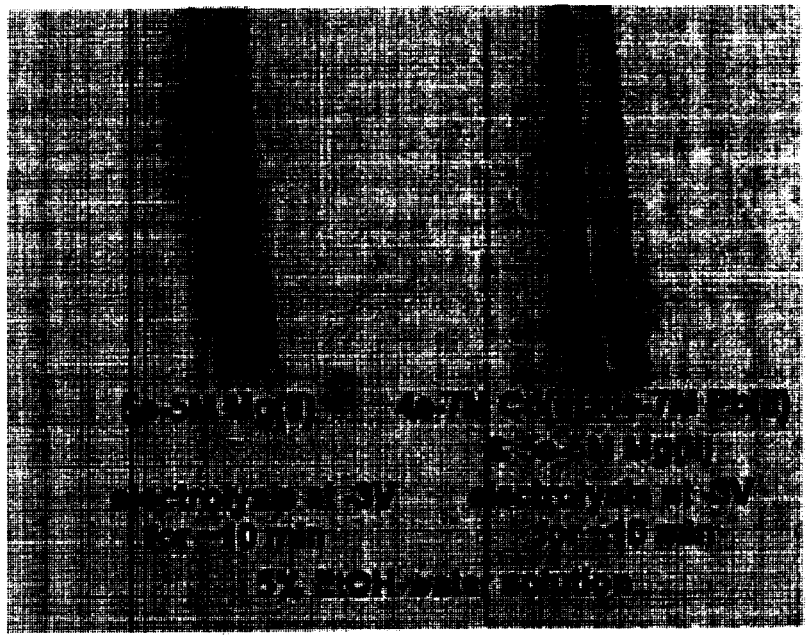
FIG. 11 is a diagram illustrating the results of simultaneously detecting Cd(II) and Pb(II) with the superhydrophobic zinc sheet in the presence of Mg(II).

FIG. 11 shows the images of the superhydrophobic zinc sheets after an electric treatment in the $5\times10^{-5}$ M Mg(II) aqueous solution and the aqueous solution containing $5\times10^{-5}$ M Mg(II)+$8\times10^{-7}$ M Pb(II)+$4\times10^{-7}$ M Cd(II). Obviously, after being treated with aqueous solution of Pb(II)+Cd(II), a significant color change occurred in the superhydrophobic zinc sheet, indicating the occurrence of a large hydrophobicity-hydrophilicity change; whereas the superhydrophobic zinc sheet treated with the aqueous solution of Mg(II) did not exhibit any color change, indicating that Mg(II) could not change the surface hydrophobicity of the superhydrophobic zinc sheet. This means that the presence of Mg (II) will not interfere with the detection of Pb(II) and Cd(II) in the method of the present application. Pb(II) and Cd(II) can be simultaneously detected in the presence of Mg(II) with the lowest detection limit at least down to $1.2\times10^{-6}$ M of the total concentration of heavy metal ions.

Example 9

Simultaneous Detection of Hg(II) and Pb(II) in Aqueous Solution in the Presence of Ca(II)

The superhydrophobic zinc sheet was prepared via the following: the zinc sheet was oxidized in 8% (v/v) N,N-dimethylacetamide-water solution at 65° C. for 72 hours, taken out and washed with deionized water, then immersed into 5 mM DCT solution (with ethanol as the solvent) for 24 hours at the room temperature for self-assembly treatment to yield a superhydrophobic zinc sheet (DCT-ZnO—Zn). The whole surface of this superhydrophobic zinc sheet can serve as the detection area.

The superhydrophobic zinc sheets were immersed into 20 mL $CaCl_2$($5\times10^{-5}$M) aqueous solution containing 5% EtOH as well as 20 mL aqueous solution of $Pb(NO_3)_2$($5\times10^{-7}$M), $HgSO_4$($5\times10^{-8}$M) and $CaCl_2$($5\times10^{-5}$M) containing 5% EtOH, with the superhydrophobic zinc sheets serving as a working electrode, Pt wire serving as a counter electrode and Ag/AgCl electrode serving as a reference electrode for the detection. An electric potential of −3V was applied to the superhydrophobic zinc sheets for 10 minutes for the electric treatment, and then immersed into red ink aqueous solution to observe the change in their surfaces.

Figure 12:
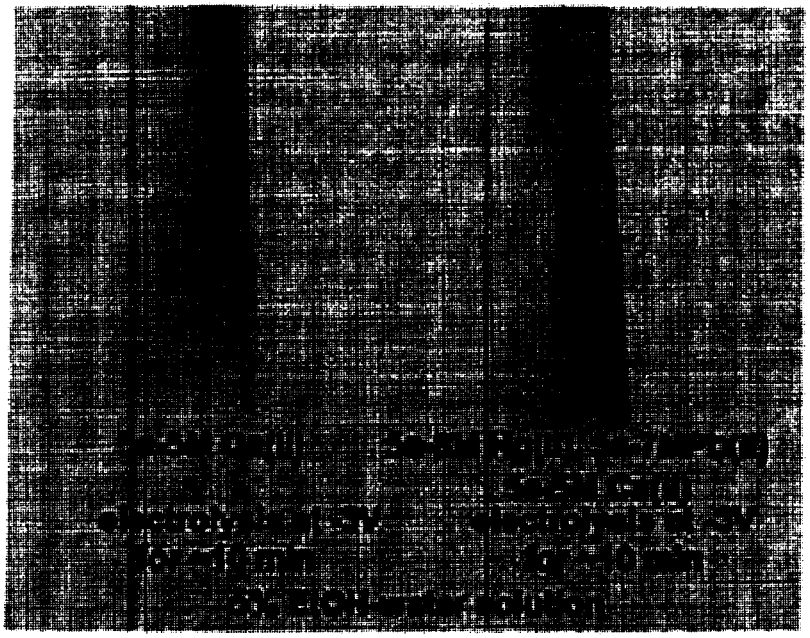
FIG. 12 is a diagram illustrating the results of simultaneously detecting Hg(II) and Pb(II) with the superhydrophobic zinc sheet in the presence of Mg(II).

FIG. 12 shows the images of the superhydrophobic zinc sheets after an electric treatment in the $5\times10^{-5}$ M Ca(II) aqueous solution and the aqueous solution containing $5\times10^{-5}$ M Ca(II)+$5\times10^{-7}$ M Pb(II)+$5\times10^{-8}$ M Hg(II). Obviously, after being treated with aqueous solution of Hg(II)+Pb(II), a significant color change occurred in the superhydrophobic zinc sheet, indicating the occurrence of a large hydrophobicity-hydrophilicity change; whereas the superhydrophobic zinc sheet treated with the aqueous solution of Ca(II) did not exhibit any color change, indicating that Ca(II) could not change the surface hydrophobicity of the superhydrophobic zinc sheet. This means that the presence of Ca(II) will not interfere with the detection of Hg(II) and Pb(II) in the method of the present application. Hg(II) and Pb(II) can be simultaneously detected in the presence of Ca(II) with the lowest detection limit at least down to $5.5\times10^{-7}$ M of the total concentration of heavy metal ions.

Although certain theories have been given in the present application, and the present application was explained based on some of these theories, a person skilled in the art will appreciate that the application does not intend to be limited by these theories.

Consecutive numbering such as (a), (b), and the like, existing in the method of the present application merely intends to be distinguishing and does not intend to indicate that no additional step exist between them. For example, an additional step may exist between step (a) and (b) and/or (b) and (c). These additional steps may be a common step in the art.

The terms "optional" and "optionally" as used herein indicate that the successive event or item (such as a step of the treatment) may or may not exist, and the disclosure includes situations in which the event or item does or does not exist.

All cited publications are herein incorporated into the present application.

It should be understood by those skilled in the art that various modifications, combinations, sub-combinations and alterations may occur depending on design requirements and other factors insofar as they are within the scope of the appended claims or the equivalents thereof.

The application is claimed as follows:

1. A method for detection of heavy metal ions in an aqueous solution, comprising:
   providing a detection material, wherein the detection material includes a hydrophilic layer which is at least partially covered by a hydrophobic layer formed from a long-chain compound selected from the group consisting of a long-chain thiol, a long-chain fatty acid, and combinations thereof, and wherein a detection area is defined by an area covered by the hydrophobic layer, and the area has a surface having an initial contact angle with water of more than or equal to about 120°;
   contacting the detection area of the detection material with an aqueous solution sample;
   determining whether the surface of the detection area of the detection material has a hydrophobicity-hydrophilicity change after the detection area is contacted with the aqueous solution sample; and deciding whether heavy metal ions exist in the aqueous solution sample according to the determination.

2. The method according to claim 1, wherein the hydrophilic layer includes a nanomaterial layer.

3. The method according to claim 1, wherein the hydrophilic layer is formed from a metal oxide.

4. The method according to claim 1, wherein the hydrophilic layer is completely covered by the hydrophobic layer.

5. The method according to claim 1, wherein the detection area has a surface having an initial contact angle with water of more than or equal to about 150°.

6. The method according to claim 1, wherein the long-chain compound is at least one selected from the long-chain thiols having 8-20 carbon atoms.

7. The method according to claim 1, wherein the long-chain compound is at least one selected from the n-alkyl thiols having 8-20 carbon atoms.

8. The method according to claim 1, wherein the long-chain compound is at least one selected from n-octyl thiol, n-dodecyl thiol, n-hexadecyl thiol and n-octadecyl thiol.

9. The method according to claim 1, wherein the method further comprises treating the detection material by applying a voltage thereto during the contacting of the detection area of the detection material with an aqueous solution sample, wherein the detection material is conductive.

10. The method according to claim 1, wherein the method further comprises immersing the detection area of the detection material into a colorant solution after contacting the area with the aqueous solution sample, and carrying out the determining of whether the surface of the detection area of the detection material has a hydrophobicity-hydrophilicity change by observing whether color change occurs in the surface of the detection area.

11. The method according to claim 1, where the heavy metal ion includes one or more of $Zn^{2+}$, $Cu^{2+}$, $Cd^{2+}$, $Pb^{2+}$, $Ag^+$, $Hg^{2+}$ and $Hg_2^{2+}$.

12. The method according to claims 1, wherein the detection material further includes a substrate which is at least partially covered by the hydrophilic layer.

13. The method according to claim 12, wherein the substrate includes a conductive substrate.

14. The method according to claim 1, wherein the detection material includes a metal substrate and a hydrophilic layer on the substrate, which is at least partially covered by a hydrophobic layer, wherein the hydrophilic layer is formed from a metal oxide and the hydrophobic layer is formed from a long-chain compound selected from a long-chain thiol, a long-chain fatty acid and combinations thereof, and wherein a detection area is defined by an area covered by the hydrophobic layer, and the detection area has a surface having an initial contact angle with water of more than or equal to about 120°.

15. The method according to claim 14, wherein the metal substrate is selected from a metal zinc substrate.

16. The method according to claim 14, wherein the metal oxide is selected from a zinc oxide.

17. The method according to claim 14, wherein the hydrophilic layer is completely covered by the hydrophobic layer.

18. The method according to claim 14, wherein the metal substrate is completely covered by the hydrophilic layer.

19. The method according to claim 1, wherein the method further comprises adding a solubilizer into the aqueous solution sample before or during the contacting of the detection area of the detection material with the aqueous solution sample.

20. The method according to claim 19, wherein the solubilizer includes a water soluble alcohol.

21. The method according to claim 19, wherein the solubilizer is at least one selected from methanol, ethanol and propanol.

* * * * *